(12) United States Patent
Falkenham

(10) Patent No.: US 11,344,490 B2
(45) Date of Patent: *May 31, 2022

(54) COMPOSITIONS AND METHODS FOR THE REMOVAL OF TATTOOS

(71) Applicant: Dalhousie University, Halifax (CA)

(72) Inventor: Alec Guy Falkenham, Halifax (CA)

(73) Assignee: Dalhousie University, Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,408

(22) Filed: Sep. 7, 2018

(65) Prior Publication Data

US 2019/0008744 A1    Jan. 10, 2019

Related U.S. Application Data

(60) Continuation of application No. 15/337,945, filed on Oct. 28, 2016, now Pat. No. 10,105,302, which is a division of application No. 14/914,929, filed as application No. PCT/CA2014/000663 on Aug. 28, 2014, now Pat. No. 9,801,799.

(60) Provisional application No. 61/871,929, filed on Aug. 30, 2013.

(51) Int. Cl.
*A61K 8/55* (2006.01)
*A61Q 1/14* (2006.01)
*A61K 8/14* (2006.01)
*A61K 8/49* (2006.01)

(52) U.S. Cl.
CPC ............... *A61K 8/55* (2013.01); *A61K 8/14* (2013.01); *A61K 8/4973* (2013.01); *A61Q 1/145* (2013.01)

(58) Field of Classification Search
CPC .......... A61K 8/55; A61K 8/4973; A61K 8/14; A61Q 1/145
See application file for complete search history.

(56) References Cited

U.S. PATENT DOCUMENTS

| | | | |
|---|---|---|---|
| 5,540,934 A | 7/1996 | Touitou | |
| 5,716,638 A | 2/1998 | Touitou | |
| 7,179,253 B2 | 2/2007 | Graham et al. | |
| 2004/0219202 A1 | 11/2004 | Fletcher et al. | |
| 2005/0201959 A1 | 9/2005 | David | |
| 2007/0081962 A1 | 4/2007 | Munshi | |
| 2007/0088414 A1 | 4/2007 | Campbell et al. | |
| 2007/0218116 A1* | 9/2007 | Schwendener | A61K 9/0019 424/450 |
| 2007/0218118 A1 | 9/2007 | Schwendener | |
| 2008/0021001 A1 | 1/2008 | Thompson et al. | |
| 2010/0145256 A1 | 6/2010 | Carter et al. | |
| 2011/0311592 A1* | 12/2011 | Birbara | A61K 9/7023 424/400 |
| 2011/0311616 A1* | 12/2011 | Smith | A61P 35/00 424/450 |
| 2012/0189678 A1* | 7/2012 | Li | A61K 9/1271 424/401 |
| 2012/0310140 A1* | 12/2012 | Kramer | A61K 9/0009 604/20 |
| 2014/0271813 A1 | 9/2014 | Richter et al. | |

FOREIGN PATENT DOCUMENTS

| | | | |
|---|---|---|---|
| EP | 0 834 301 | * | 8/1998 |
| WO | 2010/143193 | | 12/2010 |
| WO | 2011/107408 | | 9/2011 |
| WO | 2011/132826 | | 10/2011 |

OTHER PUBLICATIONS

PCT International Search Report, PCT/CA2014/000663, dated Nov. 27, 2014 (3 pages).
Cohen and Goldman, "The Adjuvant Use of Macrophage Colony Stimulating Factor in Tattoo Removal Using Laser Surgery", Medical Hypotheses, 45:83-85, 1995.
Drake, Michael T. et al., "Bisphosphonates: Mechanism of Action and Role in Clinical Practice", Mayo Clin Proc, 83(9):1032-1045, 2008.
Kessler, Sarah, "Regret That Tattoo? No Problem", downloaded from http://www.inc.com/articles/2010/02/tattoo-removal-entrepreneurs. html, 3 pages, Jan. 10, 2012.
Stratis, Athanasios et al., "Pathogenic role for skin macrophages in a mouse model of keratinocyte-induced psoriasis-like skin inflammation", The Journal of Clinical Investigation, 116(8):2094-2104, 2006.
Claassen, et al, "A new method for removal of ononuclear phagocytes from heterogeneous cell populations in vitro, using the liposome-mediated macrophage 'suicide' technique," J Immunol. Methods,134(2):153-161, 1990.
Danenberg, et al., "Liposomal Alendronate Inhibits Systemic Innate Immunity and Reduces In-Stent Neointimal Hyperplasia in Rabbits," Circulation 2003, 108(22):2798-2804.
Extended European Search Report, EP 14848935.6, dated Jan. 9, 2017 (7 pages).

(Continued)

*Primary Examiner* — Gollamudi S Kishore
(74) *Attorney, Agent, or Firm* — Honigman LLP; Fernando Alberdi; Jonathan P. O'Brien

(57) ABSTRACT

The present invention provides a method for removing a tattoo in a region of skin the method comprises administering to a least a portion of the tattoo a composition comprising an effective amount of a bisphosphonate and at least one pharmaceutically acceptable excipient to at least cause fading of the tattoo in said region.

15 Claims, 12 Drawing Sheets

(56) References Cited

OTHER PUBLICATIONS

Van Rooijen N., "The liposome-mediated macrophage 'suicide' technique," J. Immunol. Methods, 124(1):1-6, 1989.
Van Rooijen, et al., "Liposome mediated depletion of macrophages: mechanism of action, preparation of liposomes and applications," J. Immunol. Methods, 174(1-2):83-93,1994.
Jain, et al.," Transfersomes—A Novel Vesicular Carrier of Enhanced Transdermal Delivery: Development, Characterization, and Performance Evaluation," Drug Development and Industrial Pharmacy, Aug. 10, 2003, vol. 29, No. 9, pp. 1013-1026.
Kameka, et al., "Clodronate Treatment Significantly Depletes Macrophages in Chickens," The Canadian Journal of Veterinary Research, 2014, vol. 78, pp. 274-282.
Van Rooijen, et al., "Clodronate Liposomes: Perspectives in Research and Therapeutics," J Liposome Res, 2002, vol. 12, pp. 81-94.
Van Rooijen, et al., "Liposomes for Specific Depletion of Macrophages from Organs and Tissues," Liposomes, 2010, vol. 605, pp. 189-203.
Van Rooijen, N., "Liposomes for Targeting of Antigens and Drugs: Immunoadjuvant Activity and Liposome-mediated Depletion of Macrophages," 2008, J Drug Target, vol. 16(7), pp. 529-534.

\* cited by examiner

Untreated skin 1wk

Treated skin 1wk

Untreated skin 2wk

Treated skin 2wk

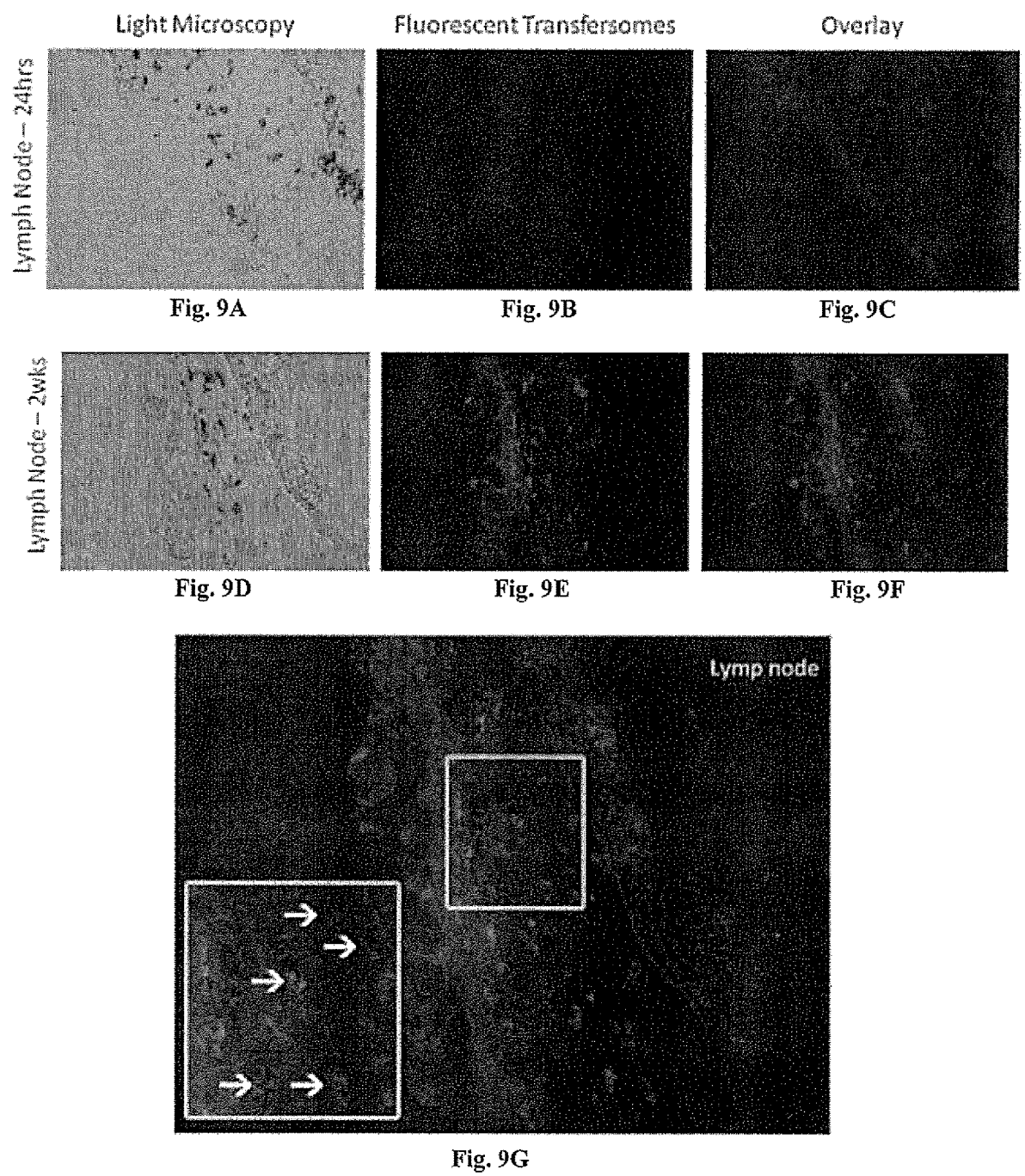

COMPOSITIONS AND METHODS FOR THE REMOVAL OF TATTOOS

CROSS REFERENCE TO PRIOR APPLICATIONS

This patent application is a continuation of U.S. patent application Ser. No. 15/337,945, filed Oct. 28, 2016, which is a divisional of U.S. patent application Ser. No. 14/914,929, filed Feb. 26, 2016, issued as U.S. Pat. No. 9,801,799 on Oct. 31, 2017, which is a 371 national phase application of PCT/CA2014/000663, filed Aug. 28, 2014, which claims the benefit of priority to U.S. Provisional Application No. 61/871,929 filed on Aug. 30, 2013, the disclosures of which are all incorporated herein by reference in their entireties.

FIELD

The present invention generally relates to compositions and their use in the treatment and removal of body art, particularly, tattoo removal.

BACKGROUND

The statements in this section merely provide background information related to the present disclosure and may not constitute prior art.

Tattoos are a popular method of body art, and there are an estimated 20-30 million tattooed individuals in the world. Approximately 50% of those who get tattoos regret all or part of their tattoos and want to have them removed completely, or faded enough to allow for re-tattooing of a new design over the old tattoo. Currently, there are no reliable, safe, consistent, or affordable methods for tattoo removal. Laser-based therapies are the standard of care and have showed promise in very specific tattoos (i.e. pigment type, size, and patient's skin color), but have several shortcomings that prevent many from seeking this treatment.

Professional tattoos are created by injecting tattoo inks with a rapidly reciprocating needle that drives ink particles into the dermis to a depth of 0.6 mm to 2.2 mm. The inks used in tattooing are derived from exogenous pigments. Pigments in tattoo ink can include iron oxides, chromium oxide, aluminum oxide, titanium oxide, barium sulfate, zinc oxide, sodium copper silicate, sodium aluminum silicate, copper carbonate, dioxazine and carbazole among other known pigment formulations. Following injection of the ink pigment particles onto a region of skin, the ink pigment particles reside in the interstitial space between dermal cells where they form large aggregates of about 100 µm to 200 µm until fibroblasts or macrophages engulf the pigment particles and internalize the tattoo ink. The size of the ink particle aggregates and the collagen network surrounding the aggregates help keep the ink pigments within the skin making the tattoo permanent, thus the difficulty with removal of tattoos.

Tattoo removal depends upon several factors including size of the tattoo, location of the tattoo, the individual's healing process, how the tattoo was applied and the length of time it has been on the skin. Tattoos naturally fade over time due to sun exposure and the ongoing immune response to foreign bodies (i.e. ink pigment particles). Laser-based therapies use high-energy light emissions at specific wavelengths to, in essence, accelerate and enhance specificity of the natural decomposition of tattoo ink by sun exposure. As tattoo inks vary in color and consequently, absorption wavelengths, lasers with different emission wavelengths are necessary to remove specific pigments, essentially requiring advanced and expensive laser treatments with sophisticated lasers that can emit several wavelengths. The high energy light decomposes the ink residing in residual bodies, allowing the natural immune response to continue. The drawbacks of laser-based therapies for tattoo removal include and are not limited to affordability, availability, reliability, consistency, associated pain and discomfort, hypo- or hyperpigmentation of the skin, and scarring. Other commonly accepted treatment modalities for tattoo removal include dermabrasion and surgical removal which may further increase the risk of adverse side effects and potential irreversible markings left in the removal process.

In addition to the more prevalent body tattoos, cosmetic tattoos or 'permanent make-up' are also skin problems that many try to remove with laser, dermabrasion and surgical treatments. In some examples of cosmetic tattoos, tattooed eyebrows, eyeliner, and lip liner are also often sought to be removed.

When working around the eye area with laser or surgical treatment, particular care must be taken to ensure that there is no eye damage, necessitating the use of protective eye shields that sit on the cornea for the removal of permanent eyeliner tattoos. The laser used to remove these pigments can also remove hair (but only temporarily) and this can be a problem when removing eyeliner, and eyebrow tattoos.

Furthermore, with cosmetic tattoos, it is possible for a shift in color to occur e.g. a pink lip liner tattoo may become dark green or black. Although, this darker color can still be treated with laser, it may not appear aesthetically pleasing during the period of removal and further increases the inconvenience, time and cost for permanent removal.

IBIS World (Tattoo Removal Practitioners Market Research Report, January 2012) values the tattoo removal market at $66 Million and determined a 21% annual growth from 2007-2012. To put the out-of-pocket cost in perspective, the average starting cost per square inch of tattoo removal can range from about $100.00 to about $150.00 (averaging approximately $125 per treatment) and it takes 6-10 treatments depending on the size and ink colors to obliterate most tattoos. It is therefore reasonable to believe, that the cost of removing a tattoo with laser therapies is far greater than the original cost of the tattoo. It follows that an alternative therapy would be desirable both from a customer and economical perspective.

For at least the reasons provided above, there is a need to provide dermatological procedures for safe, reliable and economical methods for the removal or fading of permanent tattoos.

SUMMARY

The present technology provides novel compositions for the removal and fading of tattoos applied to the skin of a mammalian subject.

In another aspect the present technology provides a method for removing a tattoo in a region of skin the method comprising: administering to a least a portion of the tattoo a composition comprising an effective amount of a bisphosphonate and at least one pharmaceutically acceptable excipient to at least cause fading of the tattoo in said region.

In one aspect, the composition is an intradermal administrable composition, a topically administrable compositions or a transdermal device. In a related aspect, the composition provides bisphosphonate particles suitable for administration in a region of skin to remove or fade a tattoo.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

In FIG. 1A, the photomicrograph illustrates the dermal layers marked with white arrows to indicate tattoo ink taken up by macrophages as seen with light microscopy.

In FIG. 1B, the photomicrograph illustrates the dermal layers marked with white arrows to indicate tattoo ink and clodronate liposomes taken up by macrophages as seen with fluorescence microscopy.

In FIG. 1C, the photomicrograph illustrates an overlay of the light microscopy structures with the presence of macrophages having phagocytosed the clodronate liposomes as seen with fluorescence microscopy.

In FIG. 1D, the photomicrograph illustrates the lymph node in treated animals 24 hours prior to sacrifice.

In FIG. 1E, the photomicrograph illustrates the lymph node viewed under fluorescence microscopy to view macrophages indicating digested clodronate liposomes in treated animals 24 hours prior to sacrifice.

Figures 1A, 1B, 1C:
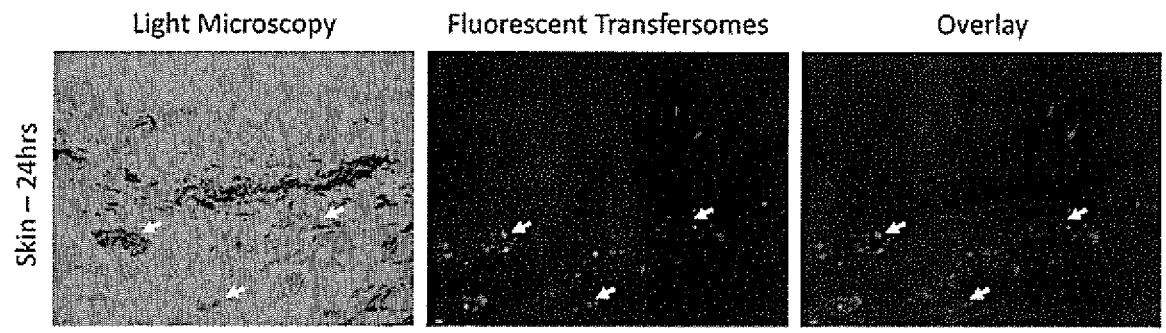
FIG. 1A depicts a photomicrograph representing skin that was treated with clodronate liposomes fluorescently labeled with a green dye.
FIG. 1B depicts a photomicrograph representing skin that was treated with clodronate liposomes fluorescently labeled with a green dye.
FIG. 1C depicts a photomicrograph representing skin that was treated with clodronate liposomes fluorescently labeled with a green dye.
Figures 1D, 1E, 1F:
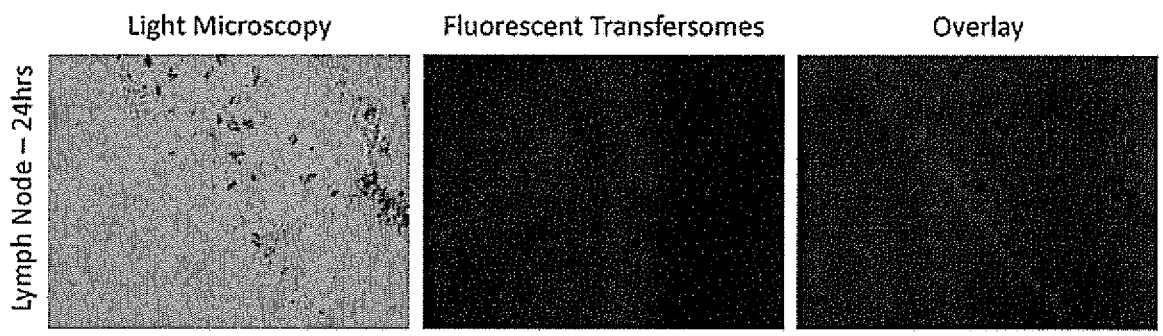
FIG. 1D depicts a photomicrograph representing a lymph node tissue section in an animal under light microscopy that was treated with clodronate liposomes fluorescently labeled with a green dye 24 hours prior.
FIG. 1E depicts a photomicrograph representing a lymph node tissue section in an animal that was treated with clodronate liposomes fluorescently labeled with a green dye 24 hours prior.

FIG. 1F depicts a photomicrograph representing a lymph node tissue section in an animal that was treated with clodronate liposomes fluorescently labeled with a green dye 2 weeks prior. In FIG. 1F, the photomicrograph illustrates the lymph node viewed as an overlay under fluorescence microscopy for presence of macrophages having phagocytosed the clodronate liposomes in treated animals 24 hours prior to sacrifice.

Figures 1G, 1H, 1I:
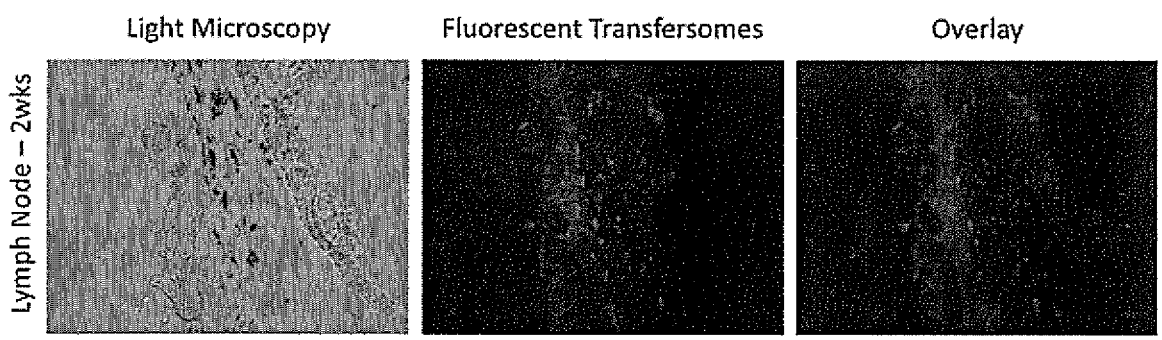

FIG. 1G depicts a photomicrograph representing a lymph node tissue section in an animal under light microscopy that was treated with clodronate liposomes fluorescently labeled with a green dye 2 weeks prior. In FIG. 1G, the photomicrograph illustrates the lymph node in treated animals 2 weeks to sacrifice.

FIG. 1H depicts a photomicrograph representing lymph node tissue section in an animal that was treated with clodronate liposomes fluorescently labeled with a green dye 2 weeks prior. In FIG. 1H, the photomicrograph illustrates the lymph node viewed under fluorescence microscopy to view macrophages indicating digested clodronate liposomes in treated animals 2 weeks prior to sacrifice.

FIG. 1I depicts a photomicrograph representing lymph node tissue section in an animal that was treated with clodronate liposomes fluorescently labeled with a green dye 2 weeks prior. In FIG. 1I, the photomicrograph illustrates the lymph node viewed as an overlay under fluorescence microscopy for presence of macrophages having phagocytosed the clodronate liposomes in treated animals 2 weeks prior to sacrifice.

Figure 2:
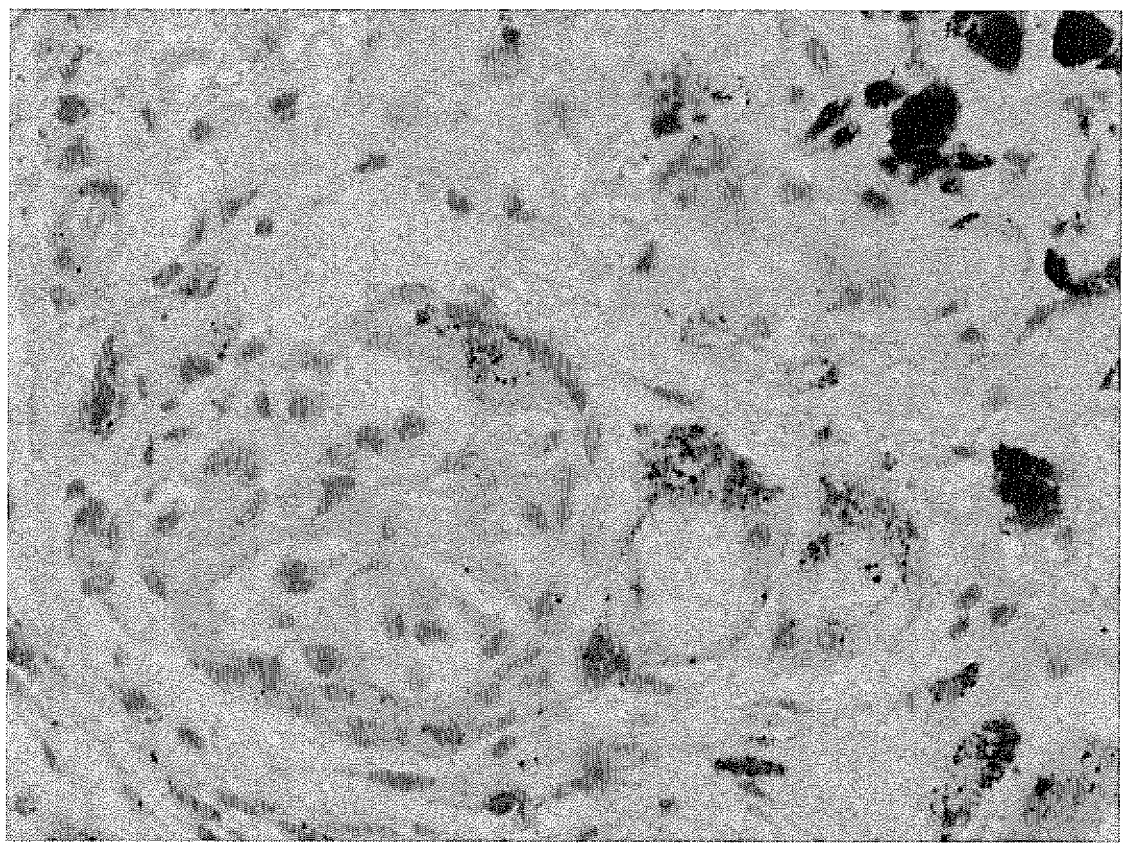

FIG. 2 depicts a photomicrograph representing dermal skin tissue in an experimental animal treated with clodronate liposomes of the present technology and an apoptosis antibody to illustrate the presence of apoptotic macrophages. As can be seen in FIG. 2, apoptotic macrophages are seen with digested tattoo ink particles.

Figure 3:
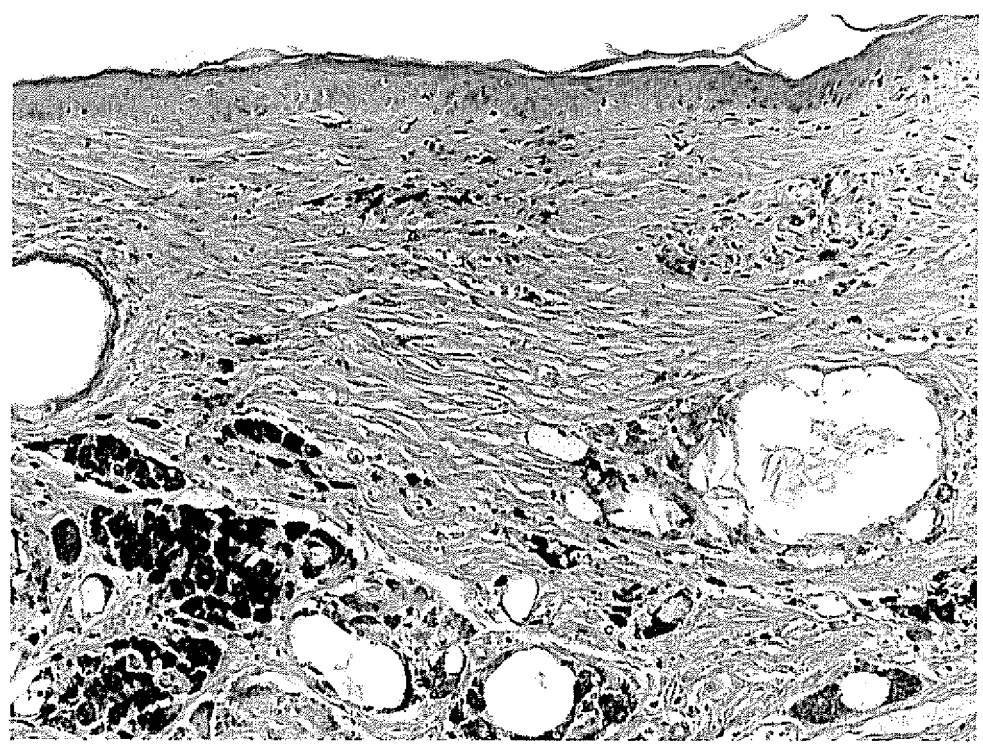

FIG. 3 depicts a photomicrograph representing dermal skin tissue in an experimental animal stained with hematoxylin and eosin that was tattooed and left to heal for 12 weeks.

Figure 4A:
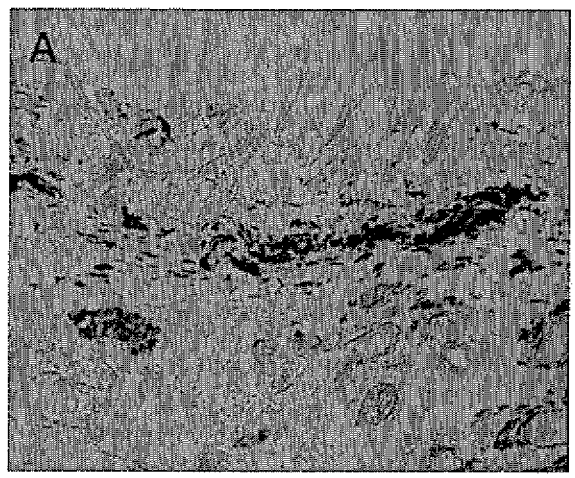

FIG. 4A depicts a photomicrograph representing a light microscopy image of a tattooed dermal skin tissue section after 24 hours in an experimental animal treated with fluorescently labeled clodronate liposomes of the present technology.

Figure 4B:
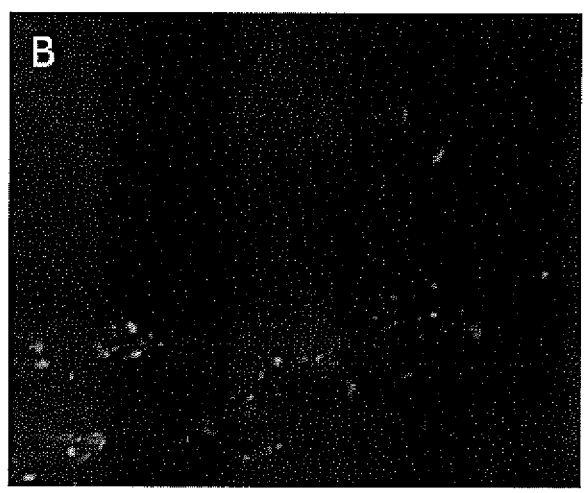

FIG. 4B depicts a photomicrograph representing a fluorescence microscopy image of a tattooed dermal skin tissue section after 24 hours in an experimental animal treated with fluorescently labeled clodronate containing liposomes of the present technology.

Figure 4C:
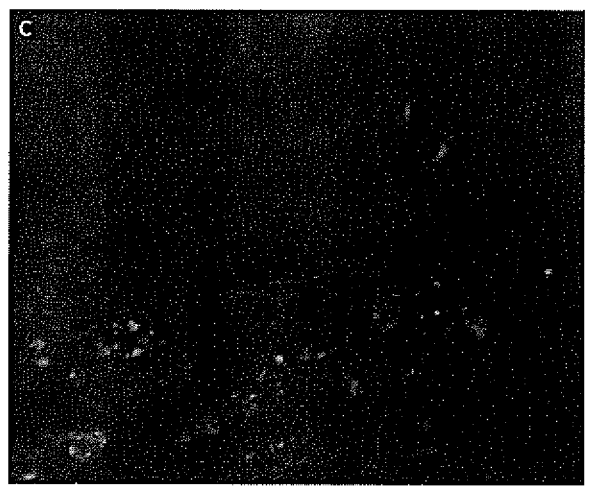

FIG. 4C depicts a photomicrograph representing the light microscopy image overlayed over the fluorescence microscopy image of the tattooed dermal skin tissue section after 24 hours in an experimental animal treated with fluorescently labeled clodronate containing liposomes of the present technology.

Figure 5A:
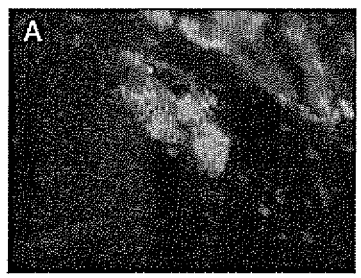

FIG. 5A depicts a photomicrograph representing a fluorescence microscopy image of a tattooed dermal skin tissue section obtained after 24 hours in an experimental animal treated with fluorescently labeled clodronate containing liposomes of the present technology.

Figure 5B:
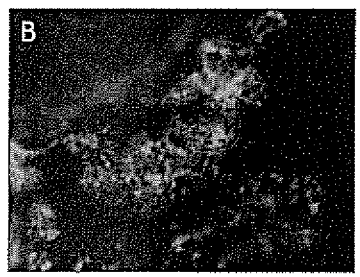

FIG. 5B depicts a photomicrograph representing a fluorescence microscopy image of a tattooed dermal skin tissue section obtained after 2 days in an experimental animal treated with fluorescently labeled clodronate containing liposomes of the present technology.

Figure 5C:
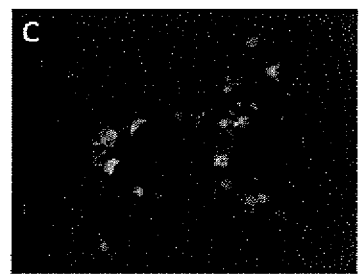

FIG. 5C depicts a photomicrograph representing a fluorescence microscopy image of a tattooed dermal skin tissue section obtained after 5 days in an experimental animal treated with fluorescently labeled clodronate containing liposomes of the present technology.

Figure 5D:
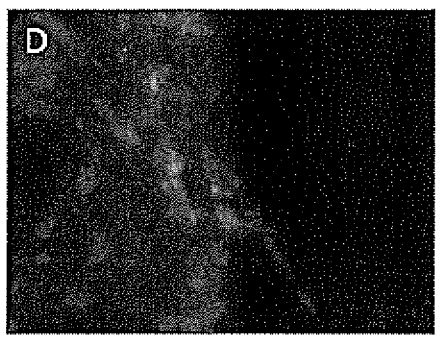

FIG. 5D depicts a photomicrograph representing a fluorescence microscopy image of a tattooed dermal skin tissue section obtained after 7 days in an experimental animal treated with fluorescently labeled clodronate containing liposomes of the present technology.

Figure 5E:

FIG. 5E depicts a photomicrograph representing a fluorescence microscopy image of a tattooed dermal skin tissue section obtained after 14 days in an experimental animal treated with fluorescently labeled clodronate containing liposomes of the present technology.

Figure 6A:
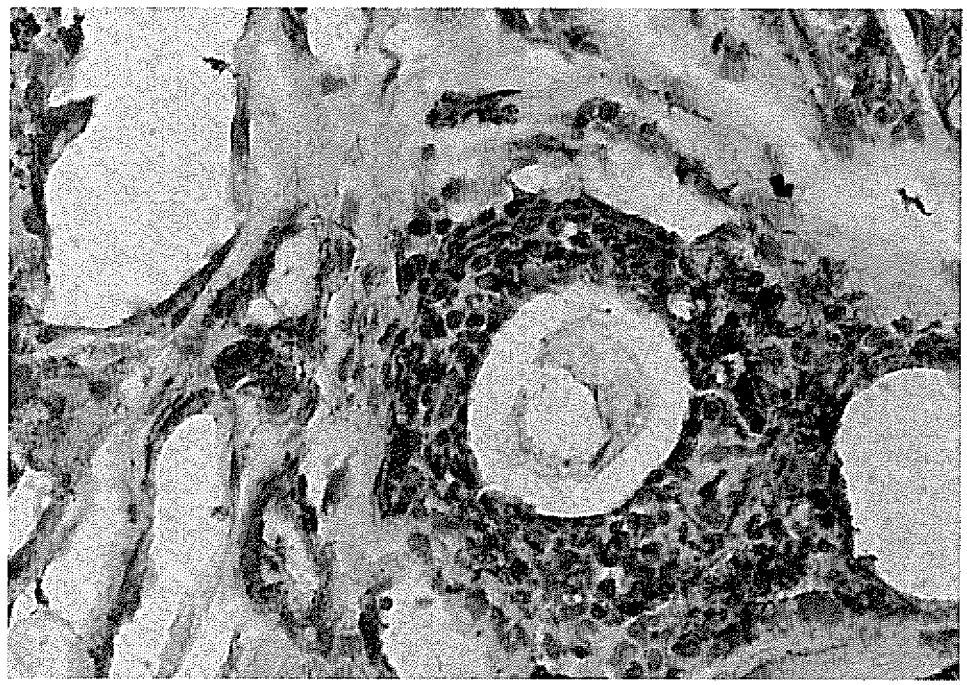

FIG. 6A depicts a photomicrograph representing a light microscopy image of a tattooed dermal skin tissue section obtained after 2 days post treatment in an experimental animal treated with clodronate containing liposomes identifying apoptosis in cells of the dermis.

Figure 6B:
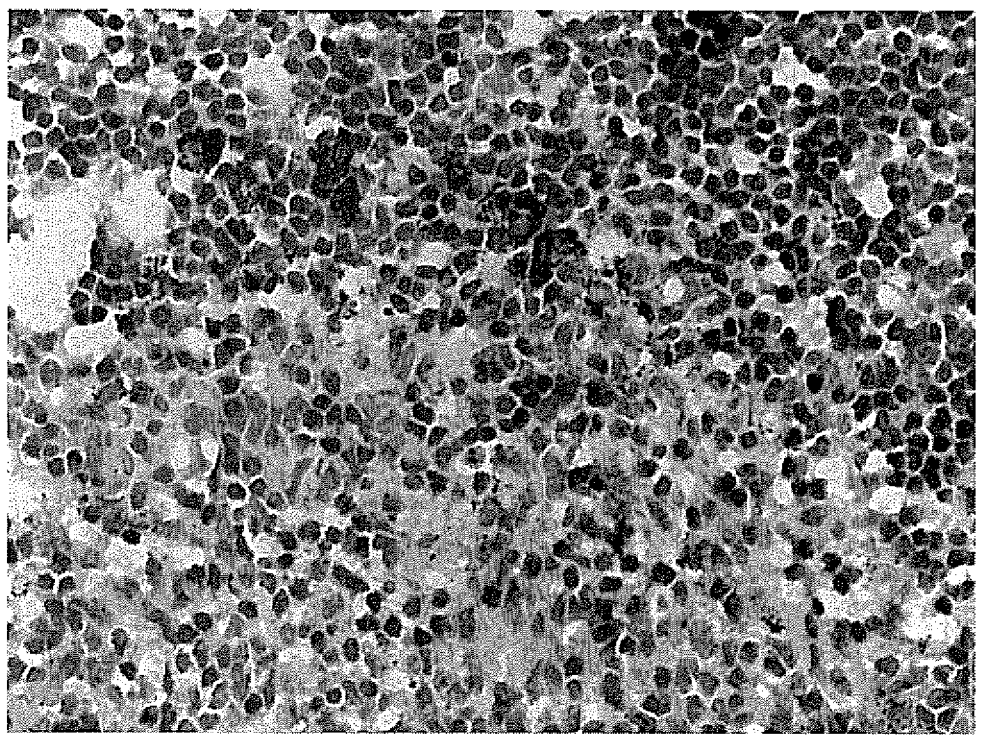

FIG. 6B depicts a photomicrograph representing a light microscopy image of a lymph node tissue section obtained after 2 days post treatment in a tattooed experimental animal treated with clodronate containing liposomes identifying apoptosis in cells of the dermis. Note the lack of TUNEL staining indicating a lack of apoptotic cells in the lymph node.

Figure 7:
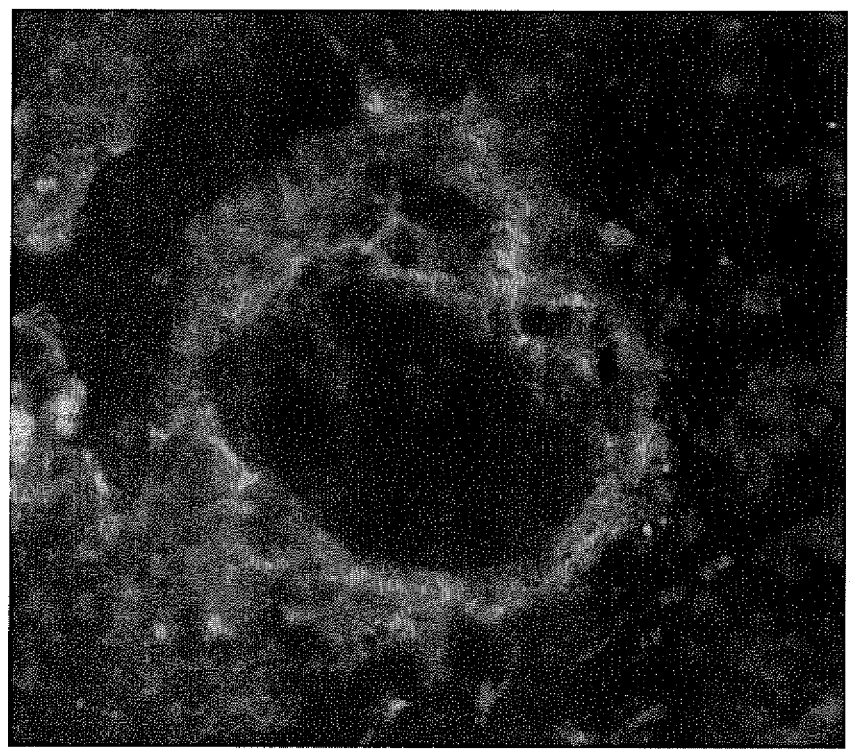

FIG. 7 depicts a photomicrograph representing a fluorescence microscopy image of a lymph node tissue section obtained after 7 days in a tattooed experimental animal treated with fluorescently labeled clodronate liposomes of the present technology. CD11b+ cells migrating from the skin to the lymph node are identified in the lymph node tissue section as shown by positive CD11b staining following treatment with the clodronate containing liposomes of the present technology.

Figure 8A:
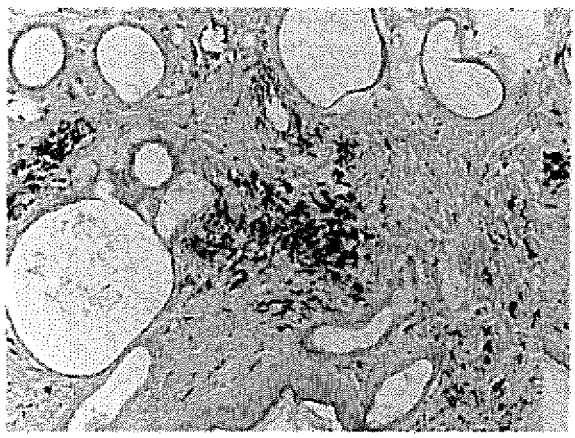

FIG. 8A depicts a photomicrograph representing a light microscopy image of an untreated tattooed dermal skin tissue section obtained after 7 days post tattoo application.

Figure 8B:

FIG. 8B depicts a photomicrograph representing a light microscopy image of a tattooed dermal skin tissue section obtained after 7 days post treatment in an experimental animal treated with clodronate containing liposomes.

Figure 8C:
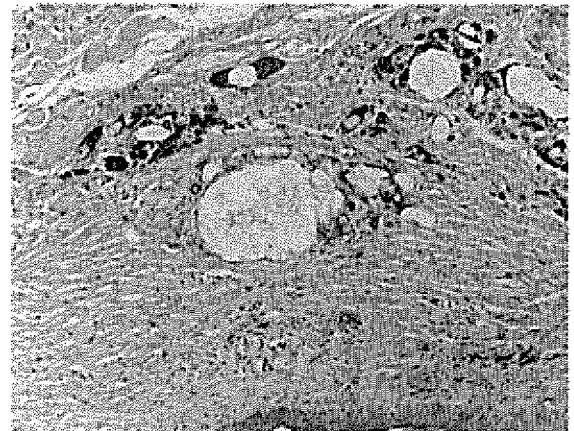

FIG. 8C depicts a photomicrograph representing a light microscopy image of an untreated tattooed dermal skin tissue section obtained after 14 days post tattoo application.

Figure 8D:
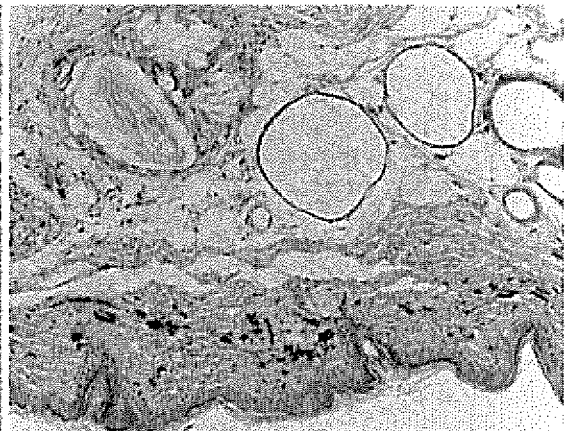

FIG. 8D depicts a photomicrograph representing a light microscopy image of a tattooed dermal skin tissue section obtained after 14 days post treatment in an experimental animal treated with clodronate containing liposomes.

FIG. 9A depicts a photomicrograph representing a light microscopy image of a lymph node tissue section obtained after 1 day post treatment in a tattooed experimental animal treated with fluorescently labeled clodronate liposomes of the present technology.

FIG. 9B depicts a photomicrograph representing a fluorescence microscopy image of a lymph node tissue section obtained after 1 day post treatment in a tattooed experimental animal treated with fluorescently labeled clodronate liposomes of the present technology.

FIG. 9C depicts a photomicrograph representing the light microscopy image overlayed over the fluorescence microscopy image of a lymph node tissue section after 1 day post treatment in a tattooed experimental animal treated with fluorescently labeled clodronate containing liposomes of the present technology.

FIG. 9D depicts a photomicrograph representing a light microscopy image of a lymph node tissue section obtained after 14 days post treatment in a tattooed experimental animal treated with fluorescently labeled clodronate liposomes of the present technology.

FIG. 9E depicts a photomicrograph representing a fluorescence microscopy image of a lymph node tissue section obtained after 14 days post treatment in a tattooed experimental animal treated with fluorescently labeled clodronate liposomes of the present technology.

FIG. 9F depicts a photomicrograph representing the light microscopy image overlayed over the fluorescence microscopy image of the lymph node tissue section after 14 days post treatment in a tattooed experimental animal treated with fluorescently labeled clodronate containing liposomes of the present technology.

FIG. 9G depicts a photomicrograph representing a fluorescence microscopy image of a lymph node tissue section obtained after 14 days post treatment in a tattooed experimental animal treated with fluorescently labeled clodronate liposomes of the present technology. Colocalization of tattoo ink and fluorescently labeled clodronate liposomes/cell debris are indicated by white arrows.

Figure 10:
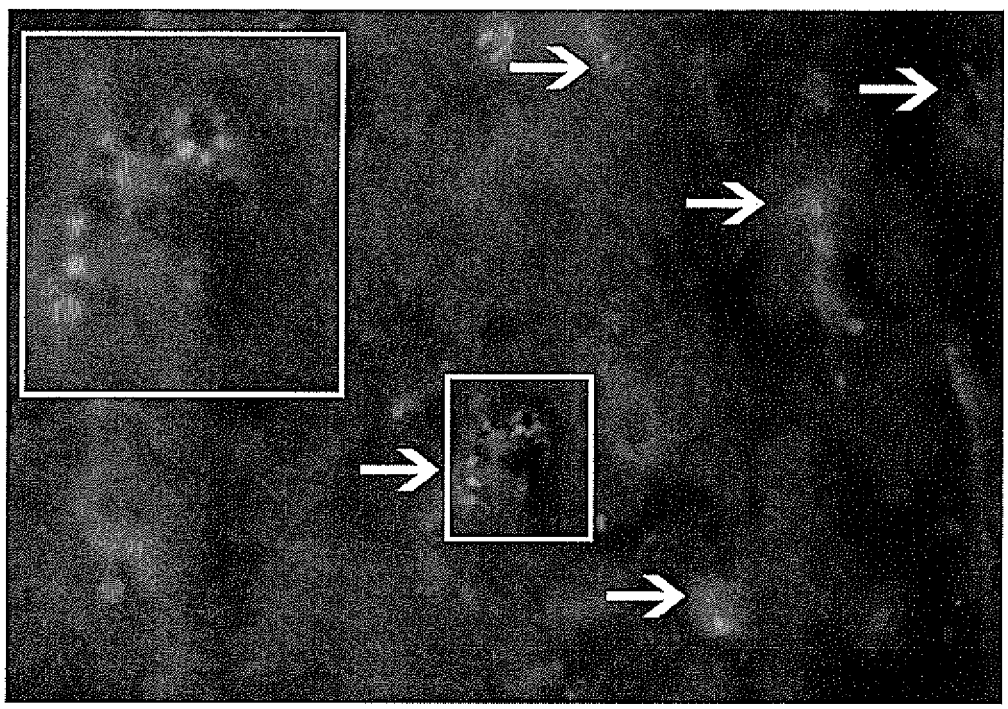

FIG. 10 depicts a photomicrograph representing a fluorescence microscopy image of a lymph node tissue section obtained after 14 days post treatment in a tattooed experimental animal treated with fluorescently labeled clodronate liposomes of the present technology and stained with phagocytic cell (monocytes and macrophage) marker CD11b. Colocalization of fluorescently labeled clodronate liposomes/cell debris and the CD11b+ staining are indicated by white arrows.

Figure 11A:
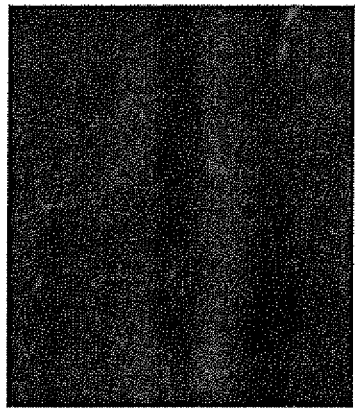
Figure 11B:
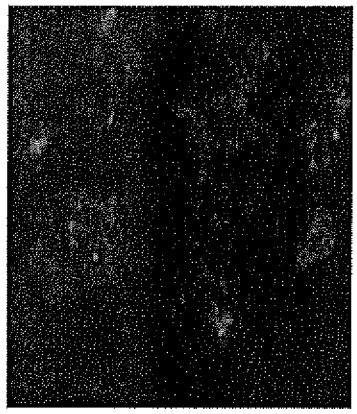

FIG. 11A depicts a photomicrograph representing a fluorescence microscopy image of a lymph node tissue section obtained after 1 day post treatment in a tattooed experimental animal treated with fluorescently labeled clodronate liposomes of the present technology FIG. 11B depicts a photomicrograph representing a fluorescence microscopy image of a lymph node tissue section obtained after 2 days post treatment in a tattooed experimental animal treated with fluorescently labeled clodronate liposomes of the present technology.

Figure 11C:
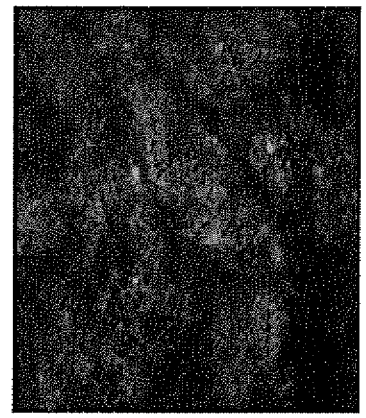

FIG. 11C depicts a photomicrograph representing a fluorescence microscopy image of a lymph node tissue section obtained after 5 days post treatment in a tattooed experimental animal treated with fluorescently labeled clodronate liposomes of the present technology.

Figure 11D:
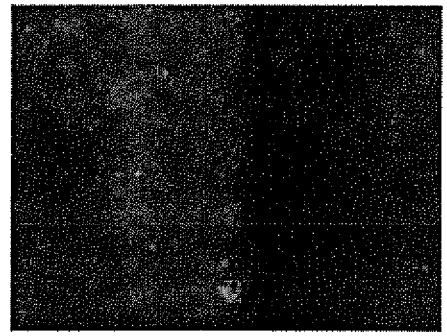

FIG. 11D depicts a photomicrograph representing a fluorescence microscopy image of a lymph node tissue section obtained after 7 days post treatment in a tattooed experimental animal treated with fluorescently labeled clodronate liposomes of the present technology.

Figure 11E:
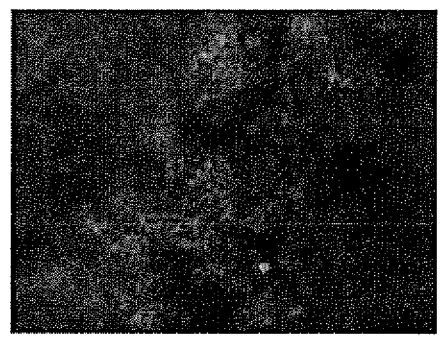

FIG. 11E depicts a photomicrograph representing a fluorescence microscopy image of a lymph node tissue section obtained after 14 days post treatment in a tattooed experimental animal treated with fluorescently labeled clodronate liposomes of the present technology.

Figure 12A:
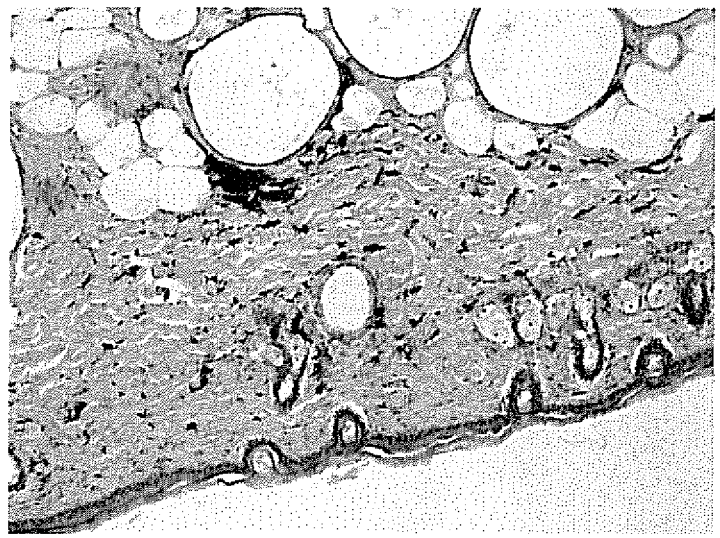
Figure 12B:
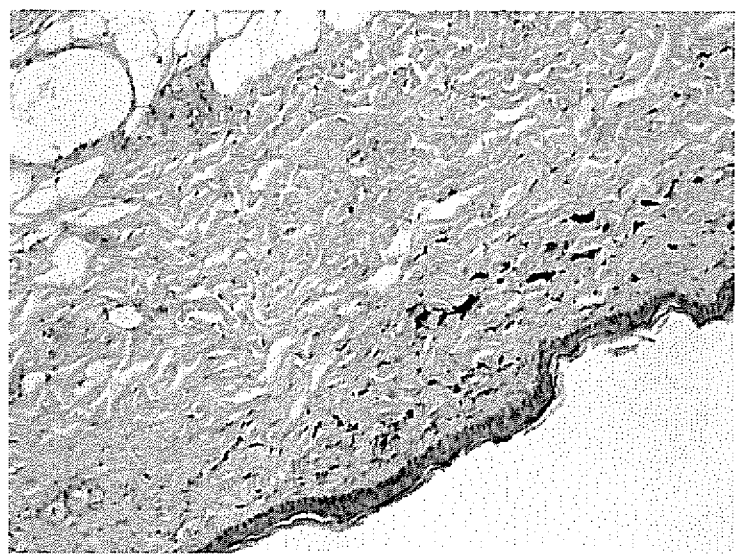

FIG. 12A depicts a photomicrograph representing a light microscopy image of a tattooed dermal skin tissue section harvested after 12 weeks treatment with a liposomal control in an experimental animal. Animals were treated once per week for 12 weeks FIG. 12B depicts a photomicrograph representing a light microscopy image of a tattooed dermal skin tissue section harvested after 12 weeks treatment with clodronate liposomes of the present technology in an experimental animal. Animals were treated once per week for 12 weeks

DETAILED DESCRIPTION

The following description is merely exemplary in nature and is not intended to limit the present disclosure, application, or uses.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made, or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of terms such as including, containing, or having, is use herein to describe and claim the present invention, the invention, or embodiments thereof, may alternatively be described using more limiting terms such as "consisting of" or "consisting essentially of" the recited ingredients.

In various embodiments, the present invention provides a method for removing a tattoo in a region of skin the method comprising: administering to a least a portion of the tattoo a composition comprising an effective amount of a bisphosphonate and at least one pharmaceutically acceptable excipient to at least cause fading of the tattoo in the region of skin.

A "tattoo" is a portion of skin in which tattoo ink has been embedded.

In various embodiments, the team "removing a tattoo" from a region of skin means extracting, for example by displacing, tattoo ink (ink pigment or ink particles) from the region of tissue underlying or surrounding the tattoo, and includes dislodging and withdrawal of the ink particles that is sufficient to cause some fading, with or without total elimination, of the tattoo in the region of skin being treated. "Removal" of a tattoo from a region of skin similarly means having extracted the tattoo ink from the tissue that is sufficient to cause some fading, with or without total elimination, of the tattoo.

As used herein the term "particle" refers to fully closed carrier molecules that may be phagocytosed by phagocytic cells, including but not limited to polymeric particles, microcapsules, liposomes, microspheres, microemulsions, nanoparticles, nanocapsules and nanospheres. In various embodiments, bisphosphonate particles are particles containing one or more bisphosphonate, diphosphonate, or acids, salts, esters, hydrates, polymorphs, hemihydrates, solvates, and derivatives thereof. The bisphosphonate, diphosphonate, or acids, salts, esters, hydrates, polymorphs, hemihydrates, solvates, and derivatives thereof is released from the bisphosphonate particle once the bisphosphonate particle has been engulfed by the phagocytic cell. In various embodiments, the bisphosphonate particles of the present technology can measure (diameter and/or length) from about 0.01 microns to about 30 microns, preferably from about 0.05 microns to about 25 microns, or from about 0.1 microns to about 20 microns ($\mu$m), or from about 0.1 microns to about 10 microns, or from about 0.1 microns to about 1 micron.

Compositions

The present inventor has identified a class of drugs, bisphosphonates, that are useful in the reduction and destruction of phagocytic cells that have taken up tattoo ink pigment and tattoo ink particles thereby reducing the amount of visible ink pigment and particles of a tattoo in the treated skin. It is believed that during and immediately after the tattoo ink has been embedded into a subject's skin, the phagocytic cell involved in the immune response engulf the tattoo ink pigment and particles and transport it to the draining lymph node via the lymphatic system. A lesser proportion of the phagocytic cells remain at the site of the tattoo in perivascular areas. These phagocytic cells store the indigestible tattoo ink pigment and particles in residual bodies where it can reside for decades, thus being responsible for the permanency of a tattoo.

The bisphosphonates as a class of drugs are thought to inhibit osteoclastic bone resorption via a mechanism that differs from that of other antiresorptive agents. Bisphosphonates are believed attach to hydroxyapatite binding sites on bony surfaces, especially surfaces undergoing active resorption. When osteoclasts begin to resorb bone that is impregnated with bisphosphonate, the bisphosphonate released during resorption impairs the ability of the osteoclasts to form the ruffled border, to adhere to the bony surface, and to produce the protons necessary for continued bone resorption. Bisphosphonates also reduce osteoclast activity by decreasing osteoclast progenitor development and recruitment and by promoting osteoclast apoptosis. In addition to their inhibitory effect on osteoclasts, bisphosphonates appear to have beneficial effects on osteoblasts. In a murine model of glucocorticoid-induced osteoporosis, bisphosphonates prevented osteocyte and osteoblast apoptosis. Bisphosphonates are commonly employed medically to inhibit bone resorption, and therefore, they find utility in the treatment of hypercalcemia, osteoporosis, metastatic bone disease, and Paget disease. Bisphosphonates all have in common the P—C—P structure, which is similar to the P—O—P structure of native pyrophosphate and differ from each other only at the two "R" groups. Some bisphosphonates, for example, neridronate, ibandronate, pamidronate, risedronate, and zoledronic acid have a nitrogen group and are called nitrogen-containing bisphosphonates in contrast to etidronate and tiludronate, which do not.

The terms "bisphosphonate" and "diphosphonate" as used herein, include acids, salts, esters, hydrates, polymorphs, hemihydrates, solvates, and derivatives thereof.

In several embodiments, bisphosphonate, diphosphonate, or acids, salts, esters, hydrates, polymorphs, hemihydrates, solvates, and derivatives thereof are used in compositions of the present technology to remove resident and non-resident phagocytic cells having digested tattoo ink pigment and particles in the perivascular area of the subject's dermal layers.

Examples of phagocytic cells include, but are not limited to cells of the mononuclear phagocytic system, including, but not limited to macrophages and circulating monocytes. Other cells capable of phagocytosis include for example neutrophils, dendritic cells, and fibroblasts. Most preferably the phagocytic cells are macrophages and/or monocytes. According to this aspect of the present invention, inhibition of phagocytic cells includes reducing the number of, eliminating (i.e., killing), retarding the proliferation of and/or reducing the activity of phagocytic cells (e.g. reducing the ability to phagocytose or to secrete cytokines). Pharmaceutical agents capable of inhibiting phagocytic cells are described herein below.

In various embodiments, the compositions of the present technology contain at least one bisphosphonate, diphosphonate, or acids, salts, esters, hydrates, polymorphs, hemihydrates, solvates, and derivatives thereof selected from: alendronate, cimadronate, incadronate, clodronate, etidronates, risedronate, zoledronate, ibandronate, minodronate, pamidronate, piridronate, tiludronate, olpadronate, neridronate, YH529, EB 1053 and ISA-13-1. At least one of these bisphosphonate, diphosphonate, or acids, salts, esters, hydrates, polymorphs, hemihydrates, solvates, and derivatives thereof is formulated with at least one pharmaceutically acceptable carrier, excipient or diluent to form a tattoo removal composition that can be applied to at least a portion of a tattoo by administration methods disclosed herein.

In some embodiments, the bisphosphonate, diphosphonate, or acids, salts, esters, hydrates, polymorphs, hemihydrates, solvates, and derivatives thereof can admixed with the at least one pharmaceutically acceptable carrier, excipient or diluent, or the bisphosphonate, diphosphonate, or acids, salts, esters, hydrates, polymorphs, hemihydrates, solvates, and derivatives thereof can be encapsulated in a particle, thereby forming a bisphosphonate particle. As used herein, a bisphosphonate particle can include: liposomes, nanospheres, microspheres, lipid bilayers, nanoparticles, microparticles, microcapsules, nanocapsules, and the like. The particle may have an outer wall defining an interior space that can be filled with the bisphosphonate, diphosphonate, or acids, salts, esters, hydrates, polymorphs, hemihydrates, solvates, and derivatives thereof. In some embodiments, the particle may comprise at least one biodegradable material, for example, one or more lipids (for example a liposome forming lipid), PGLA, silicon, cellulose, inorganic minerals (for example, calcium based ceramics) that degrade when taken-up or phagocytosed by a phagocytic cell. As used herein, the term phagocytosis also encompasses forms of endocytosis, including but not limited to pinocytosis, receptor-mediated endocytosis and other cellular means for absorbing/internalizing tattoo ink pigment or ink particles material in the dermal layers of the skin.

Dosage amount of the bisphosphonate, diphosphonate, or acids, salts, esters, hydrates, polymorphs, hemihydrates, solvates, and derivatives thereof and interval may be adjusted individually to provide skin intradermal levels of the bisphosphonate, diphosphonate, or acids, salts, esters, hydrates, polymorphs, hemihydrates, solvates, and derivatives thereof that are sufficient to induce the biological effect (effective concentration, EC). The EC will vary for each preparation, but can be estimated from in vitro data. Dosages necessary to achieve the EC will depend various factors related to the subject being treated and route of administration. Detection assays can be used to determine plasma concentrations of the liposomes and/or levels of the administered bisphosphonate, diphosphonate, or acids, salts, esters, hydrates, polymorphs, hemihydrates, solvates, and derivatives thereof.

In some embodiments, the compositions of the present technology may be administered to a region of skin using an injectable means. In some embodiments, an injectable composition can comprise bisphosphonate particles containing at least one bisphosphonate, diphosphonate, or acids, salts, esters, hydrates, polymorphs, hemihydrates, solvates, and derivatives thereof and at least one pharmaceutically acceptable excipient. In various embodiments, bisphosphonate particles can include liposomes, nanospheres, microspheres, lipid bilayers, nanoparticles, microparticles, microcapsules, nanocapsules, and the like.

According to this aspect of the present technology, bisphosphonate particles are prepared so that the size of the bisphosphonate particle is large enough to essentially be internalized by phagocytosis, thus directing the compositions of the present technology specifically to phagocytic cells. Bisphosphonate particles ranging from about 0.01 μm to about 5.0 μm, preferably from about 0.05 μm to about 1 μm can be employed in the present methods. In some embodiments, bisphosphonate, diphosphonate, or acids, salts, esters, hydrates, polymorphs, hemihydrates, solvates, and derivatives thereof containing particles are targeted directly to phagocytic cells in the dermal layers of the subject's skin are preferably in the size range of 0.02-2.5 μm, more preferably 0.05-1.0 μm and more preferably 0.07-0.7 μm.

The bisphosphonate particle may be provided in any suitable form including but not limited to a solution, a suspension, an emulsion, or any form of mixture. The bisphosphonate particle may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a foam, a solution, a suspension, a dispersion, an emulsion, a microemulsion, a paste, a powder, a solid stick (e.g., wax- or petroleum-based sticks), a wipe, an oil, a lotion, and the like. In one particular embodiment, the bisphosphonate particle is provided in a cream formulation suitable for topical administration. In another embodiment, the bisphosphonate particle is provided as an injectable formulation, for example, an intradermal formulation.

In various embodiments, the bisphosphonate particle can comprise one or more bisphosphonates in admixture with a pharmaceutically acceptable excipient. Pharmaceutically acceptable excipients for use with bisphosphonate particles may include one or more of a carrier, a diluent, a binder, a lipid, for example, cholesterol, olive oil etc., a liposome forming lipid, a drug eluting polymer or monomer, a skin penetration enhancer, for example a lower alcohol (e.g. methanol, ethanol, n-propanol, isopropanol, or combinations thereof), a chelating agent, a surfactant, an emulsifying agent, a thickening agent, a pH modifier, a pain reliever, an antibiotic, an anti-inflammatory agent, an anesthetic, a steroid, and a chelating agent (for example: ethylene diaminetetraacetate (EDTA), desferrioxamine, clioquinol, ethylene glycol tetraacetic acid (EGTA), small hydrophobic chelators such as phenanthroline or bipyridine, hexadentate iron chelator and deferoxamine (also known as desferrioxamine, desferoxamine, DFO, DFOA or desferal).

In a specific embodiment, the bisphosphonate particle is a liposome containing one or more bisphosphonate, diphosphonate, or acids, salts, esters, hydrates, polymorphs, hemihydrates, solvates, or derivatives thereof. In this embodiment, liposomes useful in the present technology can include any synthetic structure (unilamellar, or multilamellar vesicles) that is made with liposomal lipids in a liquid crystalline phase or a liquid gel phase, which enclose a volume of liquid comprising a bisphosphonate, diphosphonate, or acids, salts, esters, hydrates, polymorphs, hemihydrates, solvates, and derivatives thereof. In some embodiments, the liposomes may be coated (for example, with albumin) or uncoated.

In some embodiments, liposomes can include emulsions, foams, micelles, insoluble monolayers, liquid crystals, phospholipid dispersions, lamellar layers and the like. The liposomes may be prepared by any of the known methods in the art. The liposomes may be positively charged, neutral or, more preferably, negatively charged. In various embodiments, the liposome can comprise cholesterol, a liposome forming lipid and optionally, a polyionic polymer. In some of these embodiments, the liposome forming lipid selected from the group consisting of hydrogenated soy phosphatidylcholine, distearoylphosphatidylcholine, sphingomyelin, diacylglycerol, phosphatidyl ethanolamine, phosphatidylglycerol, phosphatidylserine, distearylphosphatidylcholine and distearylphosphatidyl ethanolamine and combinations thereof, In various embodiments, the liposomes of the present technology may also comprise a non-ionic surfactant. In some examples the non-ionic surfactant can include: polyoxyl 35, polyoxyl 40 hydrogenated castor oil (Cremophor RH 40), and polyoxyl 60 hydrogenated castor oil (Cremophor RH 60), as well as d-α-tocopherol, polyethylene glycol 1000 succinate, polysorbate 20, polysorbate 80, Sorbitan-monolaurate (Span 20), Sorbitan monopalmitate (Span 40); Sorbitan monostearate (Span 60); Sorbitan-monooleate (Span 80), Solutol HS 15, poloxamer 407, Labrafil M-1944CS, Labrafil M-2125CS, Labrasol, Gellucire 44/1. In some embodiments, the non-ionic surfactant is sorbitan monooleate.

As detailed above, many properties influence uptake of liposomes by phagocytic cells including, but not limited to liposome size, charge and hydrophobicity, as well as the phospholipids and non-phospholipid components of the liposome.

The liposomes may be modified in any other way to enhance their uptake by the phagocytic cells, e.g. by attaching to them molecules recognized selectively by phagocytic cells such as ligands that interact with the macrophage Fe receptor, serum proteins such as albumin, or galactosyl ligands, or inclusion of substances in the bilayer such as complement, fibronectin, lipoproteins, albumins or gamma globulin.

The liposomes may be a single lipid layer or may be multilamellar. If the agent capable of inhibiting phagocytic cells is hydrophilic, its delivery may be further improved using large unilamellar vesicles because of their greater internal volume. Conversely, if the agent is hydrophobic, its delivery may be further improved using multilamellar vesicles. Alternatively, the agent capable of down-regulating phagocytic cells (e.g. oligonucleotide) may not be able to penetrate the lipid bilayer and consequently would remain adsorbed to the liposome surface. In this case, increasing the surface area of the liposome may further improve delivery of the therapeutic agent. Suitable liposomes in accordance with the invention are preferably non-toxic liposomes such as, for example, those prepared from any one or more of phosphatidylcholine, distearoylphosphatidylcholine, sphingomyelin, diacylglycerol, phosphatidyl ethanolamine, phosphatidylglycerol, distearylphosphatidylcholine and distearylphosphatidyl ethanolamine, and cholesterol. The diameter of the liposomes used preferably ranges from about 0.05-25 microns, for example, from about 0.1 microns to about 10 microns, or from about 0.08 to about 1.0 micron. However, other liposome size or diameter ranges suitable for phagocytosis by phagocytic cells may also be used, and can vary greatly between cell types, such as monocytes and macrophages. In some illustrative embodiments, the liposomes can range in diameters from between, for example, 0.01 micron to about 20 microns, or for example, from about 0.1 micron to about 10 microns, or from about 0.008 microns to about 1 micron. For sizing liposomes, homogenization may be used, which relies on shearing energy to fragment large liposomes into smaller ones. Homogenizers, which may be conveniently used, include microfluidizers produced by Microfluidics of Boston, Mass. In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

In some embodiments, the liposomes of the present technology comprise a bisphosphonate, for example, clodronate, encapsulated in a liposome made from hydrogenated soy phosphatidylcholine as the liposome forming lipid. The clodronate liposomes may also contain sorbitan monooleate. Methods for making clodronate containing liposomes are known, for example, as provided in Van Rooijen, N, Sanders, A. (1994) Liposome mediated depletion of macrophages: mechanism of action, preparation of liposomes and applications J. Immunol. Methods 174:83-93, the disclosure of which is hereby incorporated by reference in its entirety. In some embodiments, Clodronate-liposomes can be produced by admixture of a liposome forming lipid with cholesterol and a solution of clodronate (ranging from about 0.1 to about 1.5 M) and sonicating the admixture gently. The resultant liposomes can then be dialyzed, centrifuged, or otherwise, washed to remove free clodronate prior to administration or formulation into a topical, transdermal or injectable dose. In some embodiments, injection ready clodronate liposomes (multilamellar clodronate encapsulated liposomes) are commercially available from Encapsula NanoSciences, (Brentwood, Tenn. USA).

The amount of a composition to be administered will, of course, be dependent on the subject being treated, the severity of the affliction, the manner of administration, the judgment of the prescribing physician, etc. The concentration of bisphosphonate particles in these formulations can vary widely, i.e., from less than about 0.5%, usually at or at least about it to as much as 15 or 20% by weight and will be selected primarily by fluid volumes, viscosities, etc., in accordance with the particular mode of administration selected.

In one embodiment, the entrapped, encapsulated or captured bisphosphonate used in connection with the formulations and methods of the present technology may have a concentration ranging from about 0.7M to about 0.001M. In some embodiments, the amount of the bisphosphonate relative to the amount of the particle may represent from about from less than about 0.5%, to about 20% of the particle (e.g. liposome) on a molar basis and 0.05 to 10% on a per weight basis. Described by ratio, in some embodiments, liposome particles have an encapsulated bisphosphonate to lipid ratio (on a molar basis) of about 1:3 to 1:250 and an encapsulated bisphosphonate to lipid ratio (on a per weight basis) of about 1:10 to 1:2000. In some embodiments, the molar ratio of encapsulated bisphosphonate, for example, clodronate, to lipid in the liposomal preparation can range from 1:4 to 3:4. In some embodiments, the weight ratio of bisphosphonate to lipid can range from 1:3 to 1:10. In various embodiments, the bisphosphonate particles can be formulated to produce a cream, an ointment, an aerosol formulation, a non-aerosol spray, a gel, a foam, a solution, a suspension, a dispersion, an emulsion, a microemulsion, a paste, a powder, a solid stick (e.g., wax- or petroleum-based sticks), a wipe, an oil, a lotion, such that when administered to a region of skin, wither through a topical application, a transdermal device, such as a patch or injected intradermally, the administered dose of the bisphosphonate particle formulation provides from about 1 nanogram of bisphosphonate per 50 micrograms of intradermal tissue to about 25 micrograms of bisphosphonate per 50 micrograms of tissue on a per weight basis. In other embodiments, the formulations of the present technology comprise from about 2% to about 20% (% wt/vol.) of the liposomes, wherein the ratio of bisphosphonate to lipid in the liposomes ranges from 1:3 to 1:250 on a per weight basis.

In some embodiments, the various liposomal compositions comprise liposomes containing 0.1 mg/mL to about 1,000 mg/mL of the bisphosphonate, for example, clodronate within the liposomes, preferably, from about 1 mg/mL to about 500 mg/mL. In some embodiments, the molar ratio of bisphosphonate, for example, clodronate, to lipid in the liposome can range from about 1:4 to about 3:4. In various embodiments, the maximum solubility of the bisphosphonate used, for example, clodronate, can range from about 100 mg/mL to about 300 mg/mL. In various embodiments, the liposome particles of the present invention entrap about 0.5% to about 5%, or from about 1% to about 2% of a bisphosphonate, for example, a clodronate solution (having a concentration of about 200 mg/mL to about 300 mg/mL). In various embodiments, the weight ratio of bisphosphonate to lipid in the prepared liposomes can range from about 1:3 to about 1:10. In some embodiments, the molar ratio of encapsulated bisphosphonate, for example, clodronate, to lipid in the liposomal preparation can range from about 1:4 to about 3:4. In some embodiments, the weight ratio of bisphosphonate, for example, clodronate to lipid can range from 1:2 to 1:10, for example, from about 1:3 to about 1:10.

Any method known in the art can be used to determine the size of the particle before administration to a patient in need thereof. For example, a Nicomp Submicron Particle Sizer (model 370, Nicomp, Santa Barbara, Calif.) utilizing laser light scattering can be used. Other methods of sizing particles are also known in the art.

Determination of the optimal size, formulation and/or amount, of a particle to be engulfed by a phagocytic cell may be determined using procedures known in the art such as the assays described in U.S. Pat. Appl. No. 20040266734 and U.S. Pat. Appl. No. 20040266734; and in Danenberg et al., Journal of cardiovascular pharmacology 2003, 42:671-9; Circulation 2002, 106:599-605; Circulation 2003, 108:2798-804. In an in vitro screening assay, liposome uptake can be visually inspected using in-vitro tissue culture of macrophages. The phagocytic cells may be obtained from an established cell line or isolated from an individual as a primary cell line. In an in vivo assay, bisphosphonate particles can be administered to a test subject (e.g. an experimental subject, a mouse, or a rabbit) and after a set amount of time, tissues may be removed and examined using confocal microscopy for evidence of phagocytic cell ingestion of the bisphosphonate particles and phagocytic cell depletion. Similarly, depletion of phagocytic cells containing ink pigment or particles may similarly be visualized using confocal microscopy.

Typically, particles of the present invention sequester the bisphosphonate, diphosphonate, or acids, salts, esters, hydrates, polymorphs, hemihydrates, solvates, and derivatives thereof, capable of inhibiting phagocytic cells for a sufficient time to enhance delivery of the bisphosphonate, diphosphonate, or acids, salts, esters, hydrates, polymorphs, hemihydrates, solvates, and derivatives thereof, and become bioavailable when they are digested by phagocytic cells in the perivascular area of the subject's treated skin. Furthermore, the bisphosphonate, diphosphonate, or acids, salts, esters, hydrates, polymorphs, hemihydrates, solvates, and derivatives thereof is typically released from the bisphosphonate particles when they are ingested within the target cell (e.g., the phagocytic cell) at the target site.

In addition to solutions, suspensions, dispersions, emulsion, microemulsions, pastes, powders that can be injected intradermally, the bisphosphonate particles can also be formulated and administered as topical formulations such as creams, ointments, aerosol formulations, a non-aerosol sprays, gels, foams, and any other known and medically acceptable topical formulations, which are known in the art and described in "Remington: The Science And Practice Of Pharmacy", 1577-1591, 1672-1673, 866-885 (Alfonso R. Gennaro ed. 19th ed. 1995); Ghosh, T. K.; et al. Transdermal And Topical Drug Delivery Systems (1997), both of which are hereby incorporated herein by reference.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Specific formulation is dependent upon the route of administration chosen, and the agent. In one embodiment, the composition is applied topically to a region of skin containing at least a portion of a tattoo. A topically administrable composition that can be used in embodiments of the present invention comprising a pharmaceutically acceptable carrier and a therapeutically effective amount of a bisphosphonate, diphosphonate, or acids, salts, esters, hydrates, polymorphs, hemihydrates, solvates, and derivatives thereof. The carriers useful for topical delivery of the specified compounds according to embodiments of the invention can be any carrier known in the art for topically administering pharmaceuticals, including, but not limited to, pharmaceutically acceptable solvents, such as a polyalcohol or water; emulsions (either oil-in-water or water-in-oil emulsions), such as creams or lotions; micro emulsions; gels; ointments; liposomes; nanoparticles or microparticles, powders; and aqueous solutions or suspensions. The pharmaceutically acceptable carrier one or more inactive pharmaceutically acceptable excipients, including, but not limited to, binders, carriers, diluents, suspending agents, lubricants, emulsifiers, flavorants, preservatives, dyes, and coatings.

The topically administrable composition are prepared by mixing a pharmaceutically acceptable carrier with a therapeutically effective amount of a bisphosphonate, diphosphonate, or acids, salts, esters, hydrates, polymorphs, hemihydrates, solvates, and derivatives thereof, according to known methods in the art, for example, methods provided by standard reference texts such as, Remington: The Science And Practice Of Pharmacy 1577-1591, 1672-1673, 866-885 (Alfonso R. Gennaro ed. 19th ed. 1995); Ghosh, T. K.; et al. Transdermal And Topical Drug Delivery Systems (1997), both of which are hereby incorporated herein by reference.

In one embodiment, the topically administrable composition is in the form of an emulsion. Emulsions, such as creams and lotions are suitable topical formulations for use in the invention. An emulsion is a dispersed system comprising at least two immiscible phases, one phase dispersed in the other as droplets ranging in diameter from 0.1 μm to 100 μm. An emulsifying agent is typically included to improve stability. When water is the dispersed phase and oil is the dispersion medium, the emulsion is termed a water-in-oil emulsion. When oil is dispersed as droplets throughout the aqueous phase as droplets, the emulsion is termed an oil-in-water emulsion. Emulsions, such as creams and lotions that can be used as topical carriers and their preparation are disclosed in Remington: The Science and Practice of Pharmacy 282-291 (Alfonso R. Gennaro ed. 19th ed. 1995), hereby incorporated herein by reference.

In another embodiment, the topically administrable composition is in the form of a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are disclosed in Remington: The Science and Practice of Pharmacy 1517-1518 (Alfonso R. Gennaro ed. 19th ed. 1995), hereby incorporated herein by reference.

In an embodiment, the topically administrable composition comprises an aqueous gel comprising water and a water-gelling amount of a pharmaceutically acceptable gelling agent selected from the group consisting of carbomers, glycerin polyacrylate, and mixtures thereof, and the topical composition has a physiologically acceptable pH.

Polymer thickeners (gelling agents) that may be used in compositions according to embodiments of the present invention include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably the gelling agent comprises between about 0.2% to about 4% by weight of the composition. More particularly, the preferred compositional weight percent range for "CARBOPOL®" is between about 0.5% to about 2%, while the preferred weight percent range for "NATROLSOL®" and "KLUCEL®" is between about 0.5% to about 4%. The preferred compositional weight percent range for both "HYPAN®" and "STABILEZE®" is between 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

In another preferred embodiment, the topically administrable composition is in the form of an ointment. Ointments are oleaginous semisolids that contain little if any water. Preferably, the ointment is hydrocarbon based, such as a wax, petrolatum, or gelled mineral oil. Suitable ointments for use in the invention are well known in the art and are disclosed in Remington: The Science and Practice of Pharmacy 1585-1591 (Alfonso R. Gennaro ed. 19th ed. 1995), hereby incorporated herein by reference.

In an embodiment of the present invention, the topically administrable composition comprises at least one of a cream, an emulsion, a foam, an ointment, a dispersion, a paste, a spray, a solution, an oil, or a microemulsion, wherein the topical compositions comprises a bisphosphonate particle and at least one agent selected from the group consisting of: stearic acid, sorbitan monooleate (Span80), stearyl alcohol, cetyl alcohol, ethanol, glycerin, polyethylene glycol, water, and mixtures thereof, and the topical composition has a physiologically acceptable pH.

In another embodiment, the topically administrable composition is in the form of an aqueous solution or suspension, preferably, an aqueous solution. Suitable aqueous topical formulations for use in the invention include those disclosed in (Alfonso R. Gennaro ed. 19th ed. 1995), hereby incorporated herein by reference.

The pH of the topical formulations of the invention is preferably within a physiologically acceptable pH, e.g., within the range of about 6 to about 8, more preferably, of about 6.3 to about 6.5. To stabilize the pH, preferably, an effective amount of a buffer is included. In one embodiment, the buffering agent is present in the aqueous topical formulation in an amount of from about 0.05 to about 1 weight percent of the formulation. Acids or bases can be used to adjust the pH as needed.

Tonicity-adjusting agents can be included in the aqueous topical formulations to be used in embodiments of the present invention. Examples of suitable tonicity-adjusting agents include, but are not limited to, sodium chloride, potassium chloride, mannitol, dextrose, glycerin, polyethylene glycol, and propylene glycol. The amount of the tonicity agent can vary widely depending on the formulation's desired properties. In one embodiment, the tonicity-adjusting agent is present in the aqueous topical formulation in an amount of from about 0.5 to about 0.9 weight percent of the formulation.

Preferably, the aqueous topical formulations have a viscosity in the range of from about 15 cps to about 25 cps. The viscosity of aqueous solutions of the invention can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose.

In a preferred embodiment, the aqueous topical formulation is isotonic saline comprising a preservative, such as benzalkonium chloride or chlorine dioxide, a viscosity-adjusting agent, such as polyvinyl alcohol, and a buffer system such as sodium citrate and citric acid.

The topically administrable composition can comprise pharmaceutically acceptable excipients such as those listed in Remington: The Science And Practice Of Pharmacy 866-885 (Alfonso R. Gennaro ed. 19th ed. 1995; Ghosh, T. K.; et al. Transdermal And Topical Drug Delivery Systems (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

Suitable protectives and adsorbents include, but are not limited to, dusting powders, zinc stearate, collodon, dimethicone, silicones, zinc carbonate, aloe vera gel and other aloe products, vitamin E oil, allatoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

In an embodiment of the present invention, the topically administrable composition further comprises one or more agent selected from the group consisting of a preservative, a local anesthetic and a skin humectant.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; stabilized chlorine dioxide, for example, the proprietary stabilized chlorine dioxide of BioCide International, Inc. of Norman, Okla., sold under the trademark Purogene™ or Purite™. Other suitable stabilized chlorine dioxide products include that sold under the trademark DuraKlor® by Rio Linda Chemical Company, Inc., and that sold under the trademark Antheium Dioxide® by International Dioxide, Inc. antibacterial esters, for example, esters of parahydroxybenzoic acid; and other anti-microbial agents such as chlorhexidine, chlorocresol, benzoic acid and polymyxin.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, sorbitan esters, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

The topically administrable composition according to embodiments of the present technology can include pharmaceuticals or their pharmaceutically acceptable salts, such as a bisphosphonate, diphosphonate, or acids, salts, esters, hydrates, polymorphs, hemihydrates, solvates, and derivatives thereof, and optionally one or more other pharmaceutically active ingredients, including, but not limited to, coal tar, dithranol (anthralin), corticosteroids like desoximetasone (Topicort), fluocinonide, vitamin D analogs (for example, calcipotriol), retinoids, Argan oil, psoralen, methotrexate, cyclosporine, retinoids or other synthetic forms of vitamin A, which may aid in the removal of phagocytic cells in the area of administration.

The topically administrable composition according to embodiments of the invention can further include local anesthetics and analgesics, such as camphor, menthol, lidocaine, and dibucaine, and pramoxine; antifungals, such as ciclopirox, chloroxylenol, triacetin, sulconazole, nystatin, undecylenic acid, tolnaftate, miconizole, clotrimazole, oxiconazole, griseofulvin, econazole, ketoconozole, and amphotericin B; antibiotics and anti-infectives, such as mupirocin, erythromycin, clindamycin, gentamicin, polymyxin, bacitracin, and silver sulfadiazine; and antiseptics, such as iodine, povidine-iodine, benzalkonium chloride, benzoic acid, chlorhexidine, nitrofurazine, benzoyl peroxide, hydrogen peroxide, hexachlorophene, phenol, resorcinol, and cetylpyridinium chloride.

In various embodiments, the amount of active agent in the compositions described herein (i.e. in injectable formulations, topical formulations and transdermal formulations), can range from 0.01% to 5% by weight of the bisphosphonate, diphosphonate, or acids, salts, esters, hydrates, polymorphs, hemihydrates, solvates, and derivatives thereof. For example, the composition can comprise, 0.01%, 0.05%, 0.1%, 0.2%, 0.3%, 0.4%, 0.5%, 0.6%, 0.7%, 0.8%, 0.9%, 1%, 2%, 3%, 4% 5%, 6%, 7%, 8% 9%, 10%, 12%, 14% 16%, 18%, or 20% by weight or by volume of the final composition, of the bisphosphonate, diphosphonate, or acids, salts, esters, hydrates, polymorphs, hemihydrates, solvates, and derivatives thereof.

In a preferred embodiment, the composition comprises 0.05%-20%, 0.1%40% or 0.1-5% by weight of the bisphosphonate, diphosphonate, or acids, salts, esters, hydrates, polymorphs, hemihydrates, solvates, and derivatives thereof.

In several embodiments, the compositions of the present invention can comprise from about 0.1 mg/mL to about 100 mg/mL of the bisphosphonate, diphosphonate, or acids, salts, esters, hydrates, polymorphs, hemihydrates, solvates, and derivatives thereof, and comprises at least one liposome forming lipid selected from the group consisting of hydrogenated soy phosphatidylcholine, distearoylphosphatidylcholine, sphingomyelin, diacylglycerol, phosphatidyl ethanolamine, phosphatidylglycerol, distearylphosphatidylcholine and distearylphosphatidyl ethanolamine and combinations thereof, and an emulsifier.

Methods of Use

In some embodiments, the present methods involve the administration of an effective amount of a bisphosphonate or diphosphonate, as used herein, which include acids, salts, esters, hydrates, polymorphs, hemihydrates, solvates, and derivatives thereof to a region of skin containing at least a portion of a tattoo to be removed or faded.

The methods of the present invention may be performed on any suitable subject. Suitable subjects include, but are not limited to, mammals, such as, but not limited to, humans, non-human primates, laboratory animals such as mice, rats, guinea-pigs, rabbits, hamsters, ferrets and the like, companion animals, such as dogs, cats, and stock animals such as cows, pigs, horses, sheep, goats and the like. In some embodiments, the subject is a human subject.

In some embodiments, the method of the present technology provides removal or fading of a tattoo in a region of skin, the method comprising: administering to a least a portion of the tattoo a composition comprising an effective amount of a bisphosphonate and at least one pharmaceutically acceptable excipient to at least cause fading of the tattoo in said region.

In various embodiments, the administered effective amount of a bisphosphonate and at least one pharmaceutically acceptable excipient, is done with the use of a pharmaceutically acceptable composition that provides a suitable benefit to risk ratio that is commensurate with standard medical practices for the dermatological removal of tattoos.

As stated above, useful compositions of the present methods can utilize bisphosphonate, and/or particles containing at least one bisphosphonate, or a diphosphonate, or pharmaceutically acceptable acids, salts, esters, hydrates, polymorphs, hemihydrates, solvates, and derivatives thereof. In some embodiments, bisphosphonates, when encapsulated in liposomes or microparticles, or nanoparticles in a "particle" dosage form, they are taken-up, by the phagocytic process mediated by the macrophages and monocytes, and to some extent by other cells with phagocytic activity such as fibroblasts residing in the dermal layers of the subject's skin. In one embodiment, administration of bisphosphonate particles in the form of liposomes, once inside the phagocytic cells, the liposomal structure of the liposome is disrupted and the encapsulated bisphosphonates, diphosphonate, or pharmaceutically acceptable acids, salts, esters, hydrates, polymorphs, hemihydrates, solvates, and derivatives thereof are released into the cytosol of the phagocytic cell, thereby killing the phagocytic cells in the perivascular area of the tattoo site. Since macrophages, in their normal state, are recruited to the dermal layers, they participate in phagocytosis to remove tattoo ink pigments and particles.

Without wishing to be bound to any particular theory, it is believed that the administration of the bisphosphonate compositions containing one or more bisphosphonates or diphosphonate, acids, salts, esters, hydrates, polymorphs, hemihydrates, solvates, and derivatives thereof, or particles containing one or more bisphosphonates or diphosphonate, acids, salts, esters, hydrates, polymorphs, hemihydrates, solvates, and derivatives thereof, reduce or fade the visible tattoo by depleting and/or destroying phagocytic cells that have phagocytosed tattoo ink, and/or are important in the accumulation of tattoo ink pigments and particles as foreign matter. Without wishing to be limited to any one particular theory, it is believed that destruction of these residual phagocytic cells containing tattoo ink pigment and/or ink particles in the perivascular areas of the dermis results in the tattoo ink pigment and ink particles being transported to the lymphatic nodes for further disposal resulting in the fading of the tattoo in the area treated with the compositions of the present technology.

Other cells capable of phagocytosis include for example neutrophils, dendritic cells, and fibroblasts. Most preferably the phagocytic cells are macrophages and/or monocytes. In some embodiments, the use of the compositions described herein containing one or more bisphosphonates or diphosphonates, acids, salts, esters, hydrates, polymorphs, hemihydrates, solvates, and derivatives thereof to remove macrophages and/or monocytes from the dermal layers can occur when the tattoo is freshly applied to a region of skin (i.e. within 24-72 hours) or after the tattoo has matured (from 2 weeks to 50 years).

Liposomes have the benefit of extending half-life by protecting clodronate from decomposition, while also enhancing the specificity for macrophages. Macrophages readily engulf and ingest clodronate liposomes, subsequently releasing the clodronate into the cytosol. Clodronate is incorrectly recognized by the phagocytic cell in the cell's mitochondria, ultimately leading to cell death. In turn, the pigment particles contained within the macrophages is released and fragmented and is disposed in the subject's lymph nodes.

Administration

In accordance with the present technology, a bisphosphonate, diphosphonate, or pharmaceutically acceptable acids, salts, esters, hydrates, polymorphs, hemihydrates, solvates, and derivatives thereof is administered to a region of skin containing at least a portion of a tattoo for removing or fading a tattoo in the region of skin.

The present invention thus provides the use of bisphosphonate, or diphosphonate, a complex of bisphosphonate, or diphosphonate, or a pharmaceutically acceptable acid, salt, ester, hydrate, polymorph, hemihydrate, solvate, and derivative thereof or particles containing said bisphosphonate, or diphosphonate, a complex of bisphosphonate, or diphosphonate, or a pharmaceutically acceptable acid, salt, ester, hydrate, polymorph, hemihydrate, solvate, and derivative thereof; for the preparation of a composition for removing or fading a tattoo in a region of skin. In one embodiment, the composition comprises a "particle" dosage form, wherein the bisphosphonate, or diphosphonate, or a pharmaceutically acceptable acid, salt, ester, hydrate, polymorph, hemihydrate, solvate, and derivative thereof is encapsulated, embedded, and/or adsorbed within a particle, dispersed in the particle matrix, adsorbed or linked on the particle surface, or in combination of any of these forms. The particle includes any one of liposomes, microparticles, nanoparticles, nanospheres, microspheres, microcapsules, or nanocapsules known in the art and examples described herein, or combinations thereof.

In some embodiments, the bisphosphonate containing particles may be administered in the form of an injectable intradermal solution, emulsion, suspension, dispersion and the like, or administered as a topical composition or as part of a transdermal applicator, such as a patch, to a region of skin containing at least a portion of a tattoo. In some embodiments, the compositions are formulated for administration using an injectable solution containing the inventive bisphosphonate particles. In some embodiments, the composition is injected into a region of skin comprising at least a portion of a tattoo intradermally or by intradermal delivery.

In various embodiments of the present technology, the bisphosphonate particles are delivered into the intradermal compartment or are intradermally delivered in a region of skin comprising at least a portion of a tattoo. In this manner, the bisphosphonate particles are administered into the dermis in such a manner that the bisphosphonate particles readily reach the richly vascularized papillary dermis and are taken up by the phagocytic cells residing in the perivascular areas of the papillary dermis. In some embodiments the bisphosphonate compositions of the present technology can be placed in the upper region of the dermis, i.e., the papillary dermis or in the upper portion of the relatively less vascular reticular dermis such that the agent readily diffuses into the papillary dermis.

In some embodiments, the bisphosphonate particles of the present technology can be delivered predominately at a depth of at least about 0.3 mm, more preferably, at least about 0.4 mm and most preferably at least about 0.5 mm up to a depth of no more than about 2.5 mm, more preferably, no more than about 2.0 mm and most preferably no more than about 1.7 mm. In some embodiments, liposomal bisphosphonate particles can be injected intradermally in a region of skin containing at least a portion of a tattoo to a depth from about 0.3 mm to about 1.25 mm, preferably about 1 mm from the skin's surface. Methods and devices for intradermal delivery of active agents are well known in the art. Illustrative methods for intradermal delivery of active agents to regions of skin can include direct intradermal (ID) administration. In some embodiments, administration of the compositions of the present technology to into regions of skin containing at least a portion of a tattoo can be achieved using, for example, microneedle-based injection and infusion systems, or any other means known to one skilled in the art to accurately target the intradermal compartment. Exemplary devices include those disclosed in PCT International Application Publication Nos. WO 01/02178, published Jan. 10, 2002; and WO 02/02179, published Jan. 10, 2002, U.S. Pat. No. 6,494,865, issued Dec. 17, 2002 and U.S. Pat. No. 6,569,143 issued May 27, 2003; and U.S. Publication No. 2005/0163711 A1, published Jun. 28, 2005; and all of which are incorporated herein by reference in their entirety. Micro-cannula- and microneedle-based methodologies and devices are also described in U.S. Publication No. 2002-0095134, published Jul. 18, 2002, which is incorporated herein by reference in its entirety. Standard steel cannula can also be used for intradermal delivery using devices and methods as described in U.S. Pat. No. 6,494,865, issued Dec. 17, 2002, which is incorporated herein by reference in its entirety. These methods and devices include the delivery of agents through narrow gauge (30 G or narrower) "micro-cannula" with a limited depth of penetration (typically ranging from 100 μm to 2 mm), as defined by the total length of the cannula or the total length of the cannula that is exposed beyond a depth-limiting hub feature.

In other embodiments, the bisphosphonate particles and compositions comprising the bisphosphonate particles may be formulated for topical administration using the topical formulations described herein. The topical formulations containing the bisphosphonate particles may be applied topically to the tattoo or portions thereof using an effective amount of the topical formulation as to cause at least some fading of the tattoo after one or more applications of the topical formulation as described herein.

Dosing

The term "effective amount" denotes an amount of the bisphosphonate particle containing composition, which is effective in achieving the desired therapeutic result, namely at least inducing some fading of the tattoo. The particular amount of the bisphosphonate particle containing composition that constitutes an effective amount may depend, at least in part, on one or more factors. Such factors include, but are not limited to, the particular bisphosphonate or diphosphonate, acid, salt, ester, hydrate, polymorph, hemihydrate, solvate, or derivative thereof being administered, the state of the subject's immune system (e.g., suppressed, compromised, stimulated); the route of administering the bisphosphonate particle containing composition; the age of the tattoo; the type of pigments contained within the tattoo; the skill and/or experience of the person who applied the tattoo; the overall size of the tattoo; and the desired result (i.e., reduction or complete removal). Accordingly, it is not practical to set forth generally the amount that constitutes an effective amount of a bisphosphonate or diphosphonate, acid, salt, ester, hydrate, polymorph, hemihydrate, solvate, or derivative thereof. Those of ordinary skill in the art, however, can readily determine the appropriate amount with due consideration of such factors.

In some embodiments, the methods of the present invention include administering sufficient bisphosphonate or diphosphonate, acid, salt, ester, hydrate, polymorph, hemihydrate, solvate, or derivative thereof to provide a dose of, for example, from about 100 ng/kg to about 50 mg/kg to the subject, although in some embodiments the method may be performed by administering the bisphosphonate or diphosphonate, acid, salt, ester, hydrate, polymorph, hemihydrate, solvate, or derivative thereof in a dose outside this range. In some of these embodiments, the method includes administering sufficient bisphosphonate or diphosphonate, acid, salt, ester, hydrate, polymorph, hemihydrate, solvate, or derivative thereof to provide a dose of from about 0.01 mg/kg to about 100 mg/kg to the subject, for example, a dose of from about 0.1 mg/kg to about 50 mg/kg. The artisan, by routine type experimentation should have no substantial difficulties in determining the effective amount in each case.

A suitable formulation may contain, for example, about 0.001%, about 0.002%, about 0:005%, about 0.01%, about 0.015%, about 0.02%, about 0.025%, about 0.05%, about 0.1%, about 0.25%, about 0.5%, about 0.75%, about 1%, about 2.5%, about 5%, about 7.5%, about 10%, about 15%, or about 20% active bisphosphonate, or diphosphonate, acid, salt, ester, hydrate, polymorph, hemihydrate, solvate, or derivative thereof on a (v/v) basis, for example, one or more of alendronate, cimadronate, incadronate, clodronate, etidronates, risedronate, zoledronate, ibandronate, minodronate, pamidronate, piridronate, tiludronate, olpadronate, neridronate, YH529, EB 1053 ISA-13-1 and pharmaceutically acceptable salts, esters and mixtures thereof. In one particular embodiment, the composition includes about 5% of one or more of alendronate, cimadronate, incadronate, clodronate, etidronates, risedronate, zoledronate, ibandronate, minodronate, pamidronate, piridronate, tiludronate, olpadronate, neridronate, YH529, EB 1053 ISA-13-1 and pharmaceutically acceptable salts, esters and mixtures thereof. In some embodiments, the amount of bisphosphonate in the composition ranges from about 10 mg/mL to about 500 mg/mL on a weight per volume basis.

In some embodiments of the invention, the composition of the present technology containing bisphosphonate particles may be administered, for example, from a single dose to multiple doses administered once or multiple times per day. In certain embodiments, the bisphosphonate particles appropriately formulated, may be administered from about once per week to about once per day. In one particular embodiment, the dosed composition containing bisphosphonate particles is administered once per day. In an alternative embodiment, the dosed composition containing bisphosphonate particles is administered once every other day. In some embodiments, the dosed composition is administered to a region of skin containing at least a portion of a tattoo, at least once per week, or at least twice per week, or at least once per month, or at least 5-10 times per month or at least 1-10 times per 6 months.

EXAMPLES

Example 1. Preparation of Tattoo Removal Compositions

The following methodology was used to make 5 mL of 10% lipid solution (weight:volume) for preparing a liposomal particle encapsulated with the bisphosphonate clodronate. In a round 100 mL bottom flask the following were combined: 0.5 grams of 95% soy phosphotidyl choline (sPC) (Avanti Lipids: 441601); 0.09 grams of Span80 (Sigma-Aldrich: S6760). To this mixture, 3 mL of chloroform/methanol (2:1) is added. The sPC and Span80 are dissolved in the chloroform/methanol mixture and evaporated under vacuum in rotary evaporator until uniform lipid film forms inside the flask. In a separate vessel, clodronate (i.e. selected bisphosphonate) (Sigma-Aldrich: D4434) is dissolved in 7% ethanol (EtOH) to make a 200 mg/mL concentration solution. The lipid film in the round bottom flask is hydrated with 10 mL of EtOH containing 200 mg/mL of clodronate. The flask is flushed with nitrogen and then capped. The flask is then rotated for 1 hr at room temperature (RT). The flask is then rested for at least 2 hrs (or overnight) at room temperature. The liposomes are formed by sonication of the formulation at 40 W for 20 min at 4° C. The Ruined liposomes containing clodronate are then extruded through 400 nm membrane twenty times. Subsequently, the liposomal formulation is then extruded through 200 nm membrane twenty times. The resultant extruded liposomal formulation is spun in a swinging rotor centrifuge for 8 hrs at 50,000 RPM at 10° C. The lower clear layer (i.e. free clodronate in 7% EtOH) is removed and reused for further liposomal preparation. The upper layer is resuspended in 7% EtOH. The resultant bisphosphonate particle containing formulation (clodronate liposomes) is then spun in a swinging rotor centrifuge for 1 hr at 24,000 RPM at 10° C. Again, the upper floating layer is removed and the pellet is resuspended in 5 mL of 7% EtOH for a final concentration of 10% liposomes (weight:volume). The clodronate liposomes are then aliquoted and flushed with nitrogen, capped, and sealed with Teflon tape. The clodronate liposomes are then stored at 4° C. in dark.

Example 2. Apoptosis of Ink Containing Macrophages with Clodronate Liposomes In Vivo Using an established model of tattooing in albino, hairless, immunocompetent (SKH1) mice, various formulations of clodronate encapsulated liposomes were tested. In brief, male SKH1 mice were obtained from Charles River (Boston, Mass.) at 8 weeks of age. The mice were housed at the Carleton Animal Care Facility at Dalhousie University and acclimated in the animal room for 2 week prior to use. All treatments of the mice conform to Canadian Council on Animal Care guidelines. At 10 weeks of age, mice were anesthetized with isoflurane and tattooed midscapular with two 1 $cm^2$ half-solid and half-lined tattoos 2 cm apart on each side of the spine using a 14-pt long-tapered tattoo needle (AIMS Inc., Hornell, N.Y.) on a commercial tattoo machine (AIMS Inc. Hornell, N.Y.). Tattoos were left to heal for 1 month prior to initiating treatment with the formulation.

At 1 month, the skin was wiped with $dH_2O$ and 25 µL of fluorescently-labeled ($DiO^+$) formulation was applied to a tattooed side of the midscapular region. The formulation was rubbed evenly on the area of skin using a nitrile rubber glove and then left to dry uncovered. At different time points, the animals were sacrificed by isoflurane followed by cervical dislocation. Skin and draining lymph nodes were harvested. Each skin segment and lymph node was divided in half: (1) fixed in 4% PFA overnight and transferred to Millonig's buffer until sunk in 2:1 OCT:sucrose (20%) or (2) fixed in 10% neutral-buffered formalin and paraffin embedded for general histology and apoptosis labeling.

Frozen skin were cut at 7 µm on a cryostat and stored at 4° C. until use. Frozen sections were stained for CD11b (AbD Serotec) followed by an Alexa Fluor® 555 Goat anti-rat IgG (H+L) (Invitrogen). Nuclei were labeled with Hoechst (H1399, Invitrogen).

Paraffin sections were cut at 5um and processed according to the manufacturer's protocol for the Apoptag peroxidase apoptosis kit (Millipore). F4/80, TUNEL, fluorescently labeled clodronate containing liposomes, and Hoechst will be visualized using a Zeiss Axioplan II and imaged with an AxioCam HRC Color Camera (Carl Zeiss International, Toronto, ON). Co-localization of F4/80-Alexa Fluor® 647, TUNEL-PE, and fluorescently labeled clodronate containing liposomes-DiO appear white. Tattoo ink appears opaque, thus allowing visualization of F4/80, fluorescently labeled clodronate containing liposomes, TUNEL, and the tattoo pigment.

Sections of skin from the treated mice reveal uptake of clodronate liposomes in vivo after 24 hours and after 2 weeks. In FIG. 1A, the photomicrograph illustrates the dermal layers marked with white arrows to indicate tattoo ink taken up by macrophages as seen with light microscopy, and as shown in FIG. 1B, the photomicrograph illustrates the dermal layers marked with white arrows to indicate tattoo ink and clodronate liposomes taken up by macrophages as seen with fluorescence microscopy. The liposomes injected have a fluorescent dye and are clearly seen in the dermal layers after 24 hours. These fluorescently labeled liposomes containing clodronate are taken up by resident macrophages as indicated in FIG. 1C illustrating an overlay of the light microscopy structures with the presence of macrophages having phagocytosed the clodronate liposomes as seen with fluorescence microscopy.

It is believed that phagocytic cells such as macrophages take up ink particles and proceed to transport the ink to the draining lymph node via the lymphatic system. The results shown in FIGS. 1D-F illustrate that at the first time point of 24 hours some of the ink has been transported to the lymph nodes.

However, after 2 weeks, the macrophages containing the clodronate liposomes are visibly seen transporting ink to the lymph nodes as shown in FIGS. 1G-H.

To confirm that the macrophages which have taken up the ink and the liposomes are sensitive to the apoptotic activity of the liposomal preparation administered, FIG. 2 depicts a photomicrograph representing dermal skin tissue in the mice model with clodronate liposomes of the present technology and an apoptosis antibody to illustrate the presence of apoptotic macrophages. As can be seen in FIG. 2, apoptotic macrophages are seen with digested tattoo ink particles. These results strongly suggest that the clodronate liposomes are preferentially taken up by the dermal macrophages. The macrophages containing ink particles also take up the clodronate encapsulated liposomes and undergo apoptosis which results in a reduction in the amount of ink particles present in the treated skin.

Example 3. Uptake of Foreign Ink Particles by Macrophages

The ability to induce macrophage cell death using liposomal clodronate in vitro has been demonstrated by the inventor's laboratory. An in-vivo protocol for removing tattoos can be performed as described. Pigs (at least 4 per group—4 groups, two treatment groups and two control groups) are tattooed by a professional tattoo artist, to best mimic a professionally administered tattoo on a human. The tattoo will be divided into a representative number of regions ranging from 1 to 10. A bisphosphonate particle composition comprising liposomal clodronate in 7% ethanol as described in Example 1 will be prepared. Clodronate encapsulated liposomes (test) and control liposomes (control) for two forms of administration will be prepared: (1) intradermal (injection) and (2) transdermal (cream). The tattoos will be allowed to heal prior to beginning the administration of the control and test liposomes. The control and test liposomes are administered (100 µL of the liposomal preparation intradermally or 100 mg of a cream containing 100 µL of the liposomal preparation—each administered dose containing a liposomal concentration of 10 mg/kg weight of the subject) to one or more regions of the tattooed skin at day 0, and then once daily for a period of ten days. Tattoos will be photographed each day, beginning at the initial administration and ending with cessation of treatment and then four weeks after the cessation of treatment. The photographs are taken under identical light settings. The degree of fading is visually qualitatively measured using a +, ++, +++ and ++++ scale representing: +~10% fading, ++ representing ~10-33% fading, +++ representing ~34-66% fading and ++++ representing >66% percent fading, each image compared to the tattoo image taken at day 0.

Example 4. Tattoo Ink Removal In Vivo

Male SKH1 mice were obtained from Charles River (Boston, Mass.) at 8 weeks of age. The mice were housed at the Carleton Animal Care Facility at Dalhousie University and acclimated in the animal room for 2 week prior to use. All treatments of the mice conform to Canadian Council on Animal Care guidelines. The animals were tattooed on the back with 4×4 cm longitudinal lines using Phoenix TAT2 black ink, which were then left to heal. After approximately 12 weeks of healing, the site of the tattoo was topically treated with a composition of the present invention. The topically administered treatment is a composition (25 microliters) comprised of a solution containing 33.07 mM lipid containing approximately 3 mg/mL of clodronate in a medium of 7% ethanol at pH 7.2, (hereinafter "clodronate containing liposomal composition"). Each dose of the clodronate containing liposomal composition contained 25 microliters of the clodronate containing liposomal composition was topically applied and equally spread over a 4 cm line of tattoo. The tattooed skin was treated with one dose per week, for a total of 12 doses per treatment site. Sections of tattooed skin and lymph nodes from treated and non-treated sites were removed at the following time points: t=day 1 (FIGS. 4, 5, 9, and 11), t=day 2 (FIGS. 5, 6, and 11), t=day 5 (FIGS. 5 and 11), t=day 7 (FIGS. 5, 7, 8, and 11), t=day 14 (FIGS. 5, 8, 9, 10, and 11) and t=12 weeks (FIGS. 3, and 12). Complete skin sections were removed capturing the epidermis and dermal layers of skin and further analysed with light microscopy or fluorescence staining.

Mice were tattooed and left to heal for 3 months before initiating treatment. FIG. 3 depicts a representative paraffin section of a healed tattoo stained with hematoxylin (nuclei) and eosin (cytoplasm). In the healed tattoo, the tattoo ink in the upper dermis has largely been relocated to the inner dermis. As shown in FIGS. 4A-4C, skin was topically treated with fluorescently labeled clodronate containing liposomes. As shown in FIG. 4A, light microscopy photomicrograph of the skin section shows dispersion of the tattoo skin ink throughout the reticular dermis. FIG. 4B depicts fluorescent labeled clodronate containing liposomes. FIG. 4C depicts an overlay image of FIG. 4A and FIG. 4B of skin from an animal treated with fluorescently labeled clodronate containing liposomes and harvested 24 hrs later. Tattoo pigment can be seen as opaque black. Unhealed tattoo ink can be seen in the reticular dermis. Colocalization of tattoo ink and fluorescently labeled clodronate containing liposomes can be seen in multiple areas. Image was taken at 40×.

FIGS. 5A-5E represent fluorescent photomicrograph images of skin from mice treated with fluorescently labeled clodronate containing liposomes at t=day 0 and harvested shown in FIG. 5A at t=day 1, FIG. 5B at t=day 2, FIG. 5C at t=day 5, FIG. 5D at t=day 7 and FIG. 5E at day 14. Tattoo pigment can be seen as opaque black. Colocalization of tattoo ink and fluorescently labeled clodronate containing liposomes appears to peak at 48 hrs. Images were taken at 40×.

As shown in FIGS. 6A and 6B representative (6A) skin and (6B) lymph node sections from mice treated with clodronate containing liposomal composition at t=0, harvested at day 2, and stained for TUNEL (apoptosis). TUNEL was developed with DAB (brown). Tattoo pigment can be seen as opaque black. Colocalization of tattoo ink and apoptosis can be seen in multiple cells in the skin as shown in FIG. 6A. Pigment can be seen in the lymph node, but there is a marked absence of apoptosis in the lymph node section as shown in FIG. 6B. Images were taken at 63×.

As shown in FIG. 7 a representative image of CD11b+ cell (macrophages and monocytes) efflux from the skin to the lymph nodes following dosing with fluorescently labeled clodronate containing liposomes at t=0 and harvesting at day 7. Tattoo ink appears as opaque.

In other experiments, mice were treated (or untreated) with liposomal compositions containing liposomes embedded with clodronate as described in the present examples. Mice were treated (topically) at one time with a dose of the clodronate containing liposomal preparation, and skin was harvested at either 1 week or 2 weeks post application. Skin sections were embedded in paraffin and cut at 5 microns. Slides were stained with hematoxylin (nuclei) and eosin (cytoplasm). FIGS. 8A-8D are oriented with the epidermis at the bottom. In the treated sections shown in FIGS. 8B and 8D, the tattoo ink has been mostly removed from the deeper dermal layer (mid to upper part of each photo) by 1 week and virtually completely removed by 2 weeks post application. This indicates that the ink that resides in the inner dermal layer (the "permanent" ink) is being removed in a gradual process dependent on bisphosphonate liposomal tattoo removal compositions of the present invention. As shown in FIGS. 8A and 8C, permanent tattoo ink is trapped intra and extracellularly in the inner and upper dermal layers.

In further experiments, lymph nodes from mice untreated and treated with fluorescently labeled liposomal compositions containing clodronate as described in the present example were sectioned. As shown in FIGS. 9A and 9D, lymph node sections taken after 1 day and 14 days respectively were imaged using light microscopy. In FIGS. 9B and 9E, sections of node tissue were fluorescently stained to visualize fluorescently labeled clodronate containing particles and/or cell debris. In each of the tissue staining methods, the top row illustrates photomicrographs of a section of lymph node from an animal treated 24 hrs prior to and the second row reflects node tissue obtained after 14 days of treatment. An overlay showing the tattoo ink particles relative to the fluorescently labeled liposomal compositions containing clodronate are shown in FIGS. 9C and 9F. FIG. 9G is shown as an enlargement of an image depicting 2 wk lymph node in the white box. Colocalization of tattoo ink and fluorescently labeled clodronate containing liposomes/cell debris can be seen in multiple areas, indicated by white arrows, which appears to increase with time after dosing with clodronate containing liposomes. Lymph nodes were negative for apoptosis markers, suggesting green labeling is due to cell debris and not active clodronate liposome mediated removal, and thus suggests, that clodronate containing liposome removal accelerates tattoo ink removal from the dermis to draining lymph node, as indicated by the colocalization not tattoo ink and cellular debris. Images were taken at 40×.

FIG. 10 depicts a photomicrograph of a lymph node from a representative mouse treated with fluorescently labeled clodronate containing liposomes and harvested 14 days after the initial dose. Monocyte/macrophage marker CD11b is distinguishable from other fluorescent staining and is seen to colocalize with the fluorescently labeled clodronate containing liposomes/cell debris. Tattoo ink can be seen as opaque black. Colocalization of tattoo ink and fluorescently labeled clodronate containing liposomes/cell debris can be seen in multiple areas, indicated by white arrows. Lymph nodes were negative for apoptosis markers, suggesting that the presence of green fluorescence labeling is cell debris and not active fluorescently labeled clodronate containing liposomes. Image was taken at 100×.

Representative photomicrographs are shown in FIGS. 11A-11E, depicting images of lymph node sections from mice treated with fluorescently labeled clodronate containing liposomes at t=0 and harvested at day 1 (FIG. 11A), at day 2 (FIG. 11B), at day 5 (FIG. 11C), at day 7 (FIG. 11D), at day 14 (FIG. 11E). Tattoo ink can be seen as opaque black. Colocalization of tattoo ink and fluorescently labeled clodronate containing liposomes in the lymph nodes appears to peak at 5-14 days. Images were taken at 40×.

Mice were treated weekly with a clodronate containing liposomal preparation, or liposomal control. Skin sections were subsequently harvested after 12 weeks of one time weekly dosing. Skin sections were embedded in paraffin and cut at 5 microns. Slides were stained with hematoxylin (nuclei) and eosin (cytoplasm). As shown in FIG. 12B, the skin section illustrates removal of tattoo ink from the deeper dermal layer leaving extracellular tattoo ink which is invulnerable to clodronate liposomal based ink removal. In contrast, in the representative liposomal control section, as shown in FIG. 12 B, the tattoo ink remains in both the deeper dermal layer and the upper dermis.

Results and Conclusion:

The results obtained as shown in FIGS. 3-12 illustrate that the liposomal formulation was found to penetrate the skin after being applied topically, at the tattoo site into the deeper dermis, where it was able to colocalize with areas of tattoo ink.

In addition, the clodronate containing liposomes, labeled with lipid soluble fluorescent dye, were found to be removed from the skin by day 7. While not wishing to be bound to any specific theory, it is believed that the administration of the clodronate containing liposomal formulation to a tattoo covered skin, led to the targeting of cells which had taken up the tattoo ink for apoptosis in the deeper dermis, which was consistent with the pattern of macrophage infiltration, as denoted by CD11b+ cells shown in FIG. 7. In the skin, the administration of the clodronate containing liposomal formulation was associated with a visual reduction in the amount of tattoo ink present in the deeper dermis relative to the untreated control skin as shown in FIGS. 12A and 12B. This difference was even more pronounced by 2 weeks post-treatment. Concurrently, while apoptosis was absent from the lymph nodes, there was a marked increase in fluorescence between day one and day fourteen post-treatment, consistent with removal of cells targeted in the skin by the fluorescent liposome formulation. Moreover, in the lymph nodes, CD11b+ cells colocalized with tattoo ink and the green fluorescence, which together with the absence of apoptosis, supports one likely mechanism of action for the bisphosphonate containing liposomal formulation of the present invention. Finally, by 12 weeks of weekly treatment, tattoo ink was virtually absent from the deeper dermis of treated animals relative to untreated animals. The remaining tattoo ink in the skin was largely localized to the upper dermis and was found to be extracellular.

What is claimed is:

1. A topical, transdermal or intradermal composition for removing or fading a tattoo located on a region of skin on a subject, the composition comprising a formulation for application to the region of the skin, wherein the formulation comprises liposomes composed of a free bisphosphonate, a liposome forming lipid, an emulsifier and a lower alcohol diluent, wherein the ratio of liposome forming lipid to emulsifier ranges from 80:20 to 90:10.

2. The composition of claim 1, wherein the bisphosphonate comprises: alendronate, cimadronate, incadronate, clodronate, etidronates, risedronate, zoledronate, ibandronate, minodronate, pamidronate, piridronate, tiludronate, olpadronate, neridronate, YH529, EB 1053 ISA-13-1 and pharmaceutically acceptable salts, esters and mixtures thereof.

3. The composition of claim 2, wherein the bisphosphonate is clodronate or a pharmaceutically acceptable salt or ester thereof.

4. The composition of claim 1, wherein the liposome forming lipid is selected from the group consisting of soy phosphatidylcholine, hydrogenated soy phosphatidylcholine, distearoylphosphatidylcholine, sphingomyelin, diacylglycerol, phosphatidyl ethanolamine, phosphatidylglycerol, distearylphosphatidylcholine and distearylphosphatidyl ethanolamine and combinations thereof.

5. The composition of claim 4, wherein the liposome forming lipid is soy phosphatidylcholine.

6. The composition of claim 1, wherein the emulsifier is a non-ionic surfactant.

7. The composition of claim 6, wherein the non-ionic surfactant is sorbitan monooleate.

8. The composition of claim 2, wherein the bisphosphonate is alendronate or a pharmaceutically acceptable salt or ester thereof.

9. The composition of claim 2, wherein the bisphosphonate is risedronate or a pharmaceutically acceptable salt or ester thereof.

10. The composition of claim 2, wherein the bisphosphonate is zoledronate or a pharmaceutically acceptable salt or ester thereof.

11. The composition of claim 2, wherein the bisphosphonate is ibandronate or a pharmaceutically acceptable salt or ester thereof.

12. The composition of claim 2, wherein the bisphosphonate is pamidronate or a pharmaceutically acceptable salt or ester thereof.

13. The composition of claim 1, wherein the composition is a topical formulation comprising a cream, an emulsion, a foam, an ointment, a dispersion, a paste, a spray, a solution, an oil, or a microemulsion.

14. The composition of claim 1, wherein the composition is a transdermal formulation comprising a transdermal patch.

15. The composition of claim 1, wherein the composition is an intradermal formulation comprising a solution, emulsion, suspension or dispersion.

* * * * *